(12) United States Patent
Bartkovitz et al.

(10) Patent No.: US 9,371,280 B2
(45) Date of Patent: *Jun. 21, 2016

(54) SUBSTITUTED PYRROLIDINE-2-CARBOXAMIDES

(71) Applicant: Hoffmann-La Roche Inc., Nutley, NJ (US)

(72) Inventors: David Joseph Bartkovitz, Nutley, NJ (US); Xin-Jie Chu, Shanghai (CN); George Kenneth Ehrlich, Bronx, NY (US); Jin-Jun Liu, Warren Township, NJ (US); Hanspeter Michel, Bloomfield, NJ (US); Binh Thanh Vu, North Caldwell, NJ (US); Chunlin Zhao, Shanghai (CN)

(73) Assignee: HOFFMANN-LA ROCHE INC., Nutley, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/904,153

(22) Filed: May 29, 2013

(65) Prior Publication Data

US 2013/0324531 A1 Dec. 5, 2013

Related U.S. Application Data

(60) Provisional application No. 61/653,133, filed on May 30, 2012.

(51) Int. Cl.
| C07D 207/16 | (2006.01) |
| C07D 401/12 | (2006.01) |
| C07D 405/12 | (2006.01) |
| C07F 9/572 | (2006.01) |
| C07H 17/02 | (2006.01) |
| C07D 471/04 | (2006.01) |

(52) U.S. Cl.
CPC ............ *C07D 207/16* (2013.01); *C07D 401/12* (2013.01); *C07D 405/12* (2013.01); *C07D 471/04* (2013.01); *C07F 9/5725* (2013.01); *C07H 17/02* (2013.01)

(58) Field of Classification Search
CPC .................................................... C07D 207/16
See application file for complete search history.

(56) References Cited

U.S. PATENT DOCUMENTS

| 2010/0075948 A1 | 3/2010 | Ding et al. |
| 2010/0152190 A1 | 6/2010 | Bartkovitz et al. |
| 2012/0010235 A1 | 1/2012 | Chu et al. |

FOREIGN PATENT DOCUMENTS

| WO | WO 2010031713 | * 2/2010 | ............ A61K 31/40 |
| WO | 2011098398 | 8/2011 | |
| WO | 2013135648 | 9/2013 | |

OTHER PUBLICATIONS

Silverman, R. B. (The Org. Chem. of Drug Design and Drug Action, Academic Press, Inc.: San Diego, 1992, pp. 4-51).*
The International Search Report and Written Opinion, issued on Aug. 21, 2013, in the corresponding PCT Patent Application No. PCT/EP2013/060834., pp. 8.
The English translation of the Japanese Office Action, issued on Nov. 24, 2015, in the corresponding Japanese Patent Application No. 2015-514443.
The English translation of the Chinese Office Action, issued on Dec. 1, 2015, in the corresponding Chinese Patent Application No. 201380028024.1.

* cited by examiner

*Primary Examiner* — Robert Havlin

(57) ABSTRACT

There are provided compounds of the formula

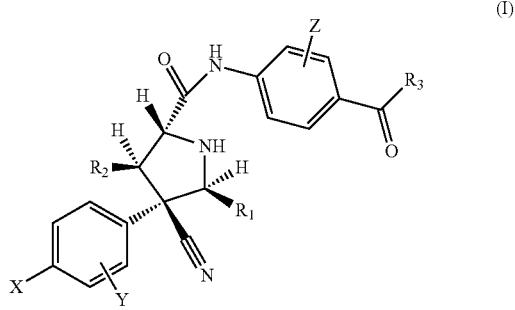

(I)

wherein X, Y, Z, $R_1$, $R_2$ and $R_3$ are as described herein and enantiomers and pharmaceutically acceptable salts and esters thereof. The compounds are useful as anticancer agents.

3 Claims, No Drawings

SUBSTITUTED PYRROLIDINE-2-CARBOXAMIDES

RELATED APPLICATION

This application is related to and claims the benefit of the filing date of U.S. Provisional Application Ser. No. 61/653,133 filed May 20, 2012.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

SUMMARY OF THE INVENTION

The present invention relates to pyrrolidine-2-carboxamide derivatives I which act as antagonists of mdm2 interactions and hence are useful as potent and selective anticancer agents. The present compounds are of the general formula

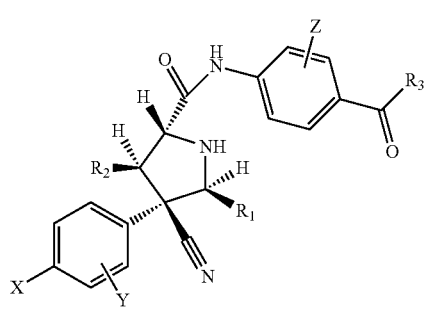

(I)

wherein X, Y, Z, $R_1$, $R_2$ and $R_3$ are as described herein and enantiomers and pharmaceutically acceptable salts and esters thereof.

DETAILED DESCRIPTION OF THE INVENTION

There are provided compounds of the formula

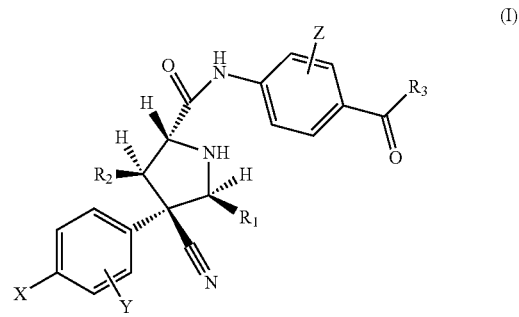

(I)

wherein

X is selected from the group consisting of H, F, Cl, Br, I, cyano, nitro, ethynyl, cyclopropyl, methyl, ethyl, isopropyl, vinyl and methoxy, Y is one to four group(s) independently selected from the group consisting of H, F, Cl, Br, I, CN, OH, nitro, lower alkyl, cycloalkyl, lower alkoxy, lower alkenyl, cycloalkenyl and lower alkynyl, Z is lower alkoxy, $R_1$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl, $R_2$ is a substituted phenyl selected from:

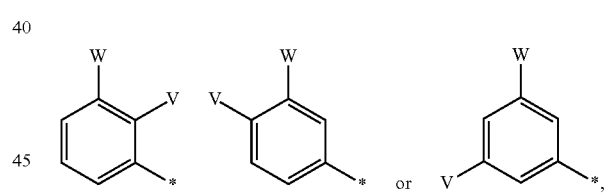

W is F, Cl or Br,

V is H or F, $R_3$ is selected from the group consisting of lower alkoxy, substituted lower alkoxy, alkylamino, dialkylamino, glucuronic acid, hexoses, aminohexoses, pyranoses, aminoglycosides, natural and unnatural amino acids, —$OCH_2C(O)N(CH_3)_2$, —$(OCH_2CH_2)_n$—OH, —$(OCH_2CH_2)_n$—$OCH_3$, —$(OCH_2CH_2)_n$—$OP(O)(OR_4)_2$, —$OCH_2C(O)$—$(OCH_2CH_2)_n$—OH, —$OCH_2C(O)$—$(OCH_2CH_2)_n$—$OCH_3$, —$NH(CH_2CH_2O)_n$—$CH_3$, —$NH(CH_2CH_2O)_n$—H, —$OCH_2C(O)NH(CH_2CH_2O)_n$—$CH_3$, —O—$R_5$, —$OCH_2$—$R_5$, $OCH_2CH_2$—$R_5$, —$OCH_2C(O)$—$R_5$, —NH$(OCH_2CH_2)_n$—$NH_2$ and —$OCH_2CH_2$-amino acid, wherein n is from 3 to 80, $R_4$ is hydrogen or benzyl, $R_5$ is selected from the group consisting of heterocycles, substituted heterocycles, dialkylamino, alkylamino and aminoalkyl alcohols, or a pharmaceutically acceptable salt or ester thereof.

Alternatively there are compounds wherein
X is selected from H, F or Cl,
Y is selected from H, F or Cl,
$R_1$ is lower alkyl or substituted lower alkyl,
$R_3$ is selected from the group consisting of lower alkoxy, substituted lower alkoxy, alkylamino, dialkylamino, glucuronic acid, hexoses, aminohexoses, pyranoses, aminoglycosides, natural and unnatural amino acids, —$OCH_2C(O)N(CH_3)_2$, —$(OCH_2CH_2)_n$—OH, —$(OCH_2CH_2)_n$—$OCH_3$, —$(OCH_2CH_2)_n$—$OP(O)(OR_4)_2$, —$OCH_2C(O)$—$(OCH_2CH_2)_n$—OH, —$OCH_2C(O)$—$(OCH_2CH_2)_n$—$OCH_3$, —$NH(CH_2CH_2O)_n$—$CH_3$, —$NH(CH_2CH_2O)_n$—H, —$OCH_2C(O)NH(CH_2CH_2O)_n$—$CH_3$, —O—$R_5$, —$OCH_2$—$R_5$, $OCH_2CH_2$—$R_5$, —$OCH_2C(O)$—$R_5$, —$NH(OCH_2CH_2)_n$—$NH_2$ and —$OCH_2CH_2$-amino acid, wherein n is from 3 to 60,
$R_4$ is hydrogen or benzyl,
$R_5$ is selected from the group consisting of heterocycles, substituted heterocycles, dialkylamino, alkylamino and aminoalkyl alcohols,
or a pharmaceutically acceptable salt or ester thereof.

Alternatively there are compounds wherein
X is selected from H, F or Cl,
Y is selected from H, F or Cl,
$R_1$ is lower alkyl or substituted lower alkyl,
$R_3$ is selected from the group consisting of lower alkoxy, substituted lower alkoxy, alkylamino, dialkylamino, glucuronic acid, hexoses, aminohexoses, pyranoses, aminoglycosides, natural and unnatural amino acids, —$OCH_2C(O)N(CH_3)_2$, —$(OCH_2CH_2)_n$—OH, —$(OCH_2CH_2)_n$—$OCH_3$, —$(OCH_2CH_2)_n$—$OP(O)(OR_4)_2$, —$OCH_2C(O)$—$(OCH_2CH_2)_n$—OH, —$OCH_2C(O)$—$(OCH_2CH_2)_n$—$OCH_3$, —$NH(CH_2CH_2O)_n$—$CH_3$, —$NH(CH_2CH_2O)_n$—H, —$OCH_2C(O)NH(CH_2CH_2O)_n$—$CH_3$, —O—$R_5$, —$OCH_2$—$R_5$, $OCH_2CH_2$—$R_5$, —$OCH_2C(O)$—$R_5$, —$NH(OCH_2CH_2)$—$NH_2$ and —$OCH_2CH_2$-amino acid, wherein n is from 3 to 45,
$R_4$ is hydrogen or benzyl,
$R_5$ is selected from the group consisting of heterocycles, substituted heterocycles, dialkylamino, alkylamino and aminoalkyl alcohols,
or a pharmaceutically acceptable salt or ester thereof.

Especially preferred are compounds selected from

2-Hydroxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 2-(2-Hydroxyethoxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 2-((S)-2-tert-butoxycarbonylamino-propionyloxy)-ethyl ester, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 2-((S)-2-amino-propionyloxy)-ethyl ester, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 2-((R)-2-tert-butoxycarbonylamino-propionyloxy)-ethyl ester, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 2-((R)-2-amino-propionyloxy)-ethyl ester, 2-(Dimethylamino)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, (2,2-Dimethyl-1,3-dioxolan-4-yl)methyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 3-Hydroxy-2-(hydroxymethyl)propyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 2-Methoxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 2-Iodoethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 2-(Di-tert-butoxyphosphoryloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 2-(Phosphonooxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, trifluoroacetate salt, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(2-hydroxy-1-methyl-ethylcarbamoyl)-2-methoxy-phenyl]-amide, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-diethylamino-ethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-methyl-piperidin-4-yl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-methyl-piperidin-4-ylmethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(4-methyl-piperazin-1-yl)-ethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid [1,2,3]triazolo[4,5-b]pyridin-3-yl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-methyl-2-morpholin-4-yl-ethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-morpholin-4-yl-ethyl ester, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(2-diethylamino-ethylcarbamoyl)-2-methoxy-phenyl]-amide, hydrochloride, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid dimethylcarbamoylmethyl ester, hydrochloride, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-morpholin-4-yl-propyl ester, hydrochloride, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid {2-methoxy-4-[2-(4-methyl-piperazin-1-yl)-ethylcarbamoyl]-phenyl}-amide, hydrochloride, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylcarbamoyl-2-methoxy-phenyl)-amide, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (2S,3R,4R,5R)-2,3,4,5,6-pentahydroxy-hexyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-tert-butoxycarbonylamino-acetoxy)-ethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-amino-acetoxy)-ethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(tert-butoxycarbonyl-methyl-amino)-acetoxy]-ethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-methylamino-acetoxy)-ethyl ester, hydrochloride, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[(S)-3-methyl-2-((S)-2-tert-butoxycarbonyl-methylamino-propionylamino)-butyryloxy]-ethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[(S)-3-methyl-2-((S)-2-methylamino-propionylamino)-butyryloxy]-ethyl ester, hydrochloride, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid methoxycarbonylmethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 3-carboxy-propyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-tert-butoxycarbonyl-ethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-carboxy-ethyl ester, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-hydrazinocarbonyl-2-methoxy-phenyl)-amide, 2S,3S,4S,5R,6S)-6-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-3,4,5-trihydroxy-tetrahydro-pyran-2-carboxylic acid; with trifluoro-acetic acid, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (2R,3S,4S,5R,6R)-3,4,5,6-tetrahydroxy-tetrahydro-pyran-2-ylmethyl ester; with trifluoro-acetic acid, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, 2-(2-{2-[2-(2-{2-[2-(2-hydroxy-ethoxy)-ethoxy]-ethoxy}-ethoxy)-ethoxy]-ethoxy}-ethoxy)-ethyl ester, trifluoroacetate salt, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, dodecaethylene glycol ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, polyethylene glycol-600 ester, trifluoroacetate salt, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, polyethylene glycol-200 ester, trifluoroacetate salt, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-dimethylamino-ethoxy)-ethyl ester, hydrochloride, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(2-hydroxy-ethoxy)-ethoxy]-ethyl ester, hydrochloride, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(2-methoxy-ethoxy)-ethoxy]-ethyl ester, hydrochloride, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-methoxy-ethoxy)-ethoxy]-ethoxy}-ethyl ester, hydrochloride, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-{2-[2-(2-hydroxy-ethoxy)-ethoxy]-ethoxy}-ethoxy)-ethyl ester, hydrochloride, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-{2-[2-(2-methoxy-ethoxy)-ethoxy]-ethoxy}-ethoxy)-ethyl ester, hydrochloride, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(2-{2-[2-(2-hydroxy-ethoxy)-ethoxy]-ethoxy}-ethoxy)-ethoxy]-ethyl ester, hydrochloride, (R)-2-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoylamino)-pentanedioic acid dimethyl ester, hydrochloride, (R)-2-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoylamino)-pentanedioic acid, hydrochloride, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid {2-methoxy-4-[methyl-((2S,3R,4R,5R)-2,3,4,5,6-pentahydroxy-hexyl)-carbamoyl]-phenyl}-amide, hydrochloride, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [2-methoxy-4-((2S,3R,4R,5S,6R)-2,4,5-trihydroxy-6-hydroxymethyl-tetrahydro-pyran-3-ylcarbamoyl)-phenyl]-amide, hydrochloride, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-hydroxyethoxy)-ethoxy]-ethoxy}-ethyl ester, hydrochloride, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-350 ester, trifluoroacetate salt, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-550 ester, hydrochloride, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, 2-[4-(2-hydroxy-ethyl)-piperazin-1-yl]-ethyl ester, dimer, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[4-(2-hydroxy-ethyl)-piperazin-1-yl]-ethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[4-(2-hydroxy-ethyl)-piperazin-1-yl]-ethyl ester, PEG-400 ester, hydrochloride salt, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[4-(2-hydroxy-ethyl)-piperazin-1-yl]-ethyl ester, mPEG-750 ester, hydrochloride salt, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(4-methyl-piperazin-1-yl)-2-oxo-ethyl ester, hydrochloride, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid carbamoylmethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-morpholin-4-yl-2-oxo-ethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid [(2,2-dimethyl-[1,3]dioxolan-4-ylmethyl)-carbamoyl]-methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (2,3-dihydroxy-propylcarbamoyl)-methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid carboxymethyl ester, (S)-2-[2-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-acetylamino]-pentanedioic acid dibenzyl ester, (S)-2-[2-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-acetylamino]-pentanedioic acid, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(2-methoxy-ethoxy)-ethoxy]-ethoxycarbonylmethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-methoxy-ethoxy)-ethoxy]-ethoxy}-ethoxycarbonylmethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid [2-(2-hydroxy-ethoxy)-ethylcarbamoyl]-methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (2-{2-[2-(2-hydroxy-ethoxy)-ethoxy]-ethoxy}-ethylcarbamoyl)-methyl ester, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(2-{2-[2-(2-amino-ethoxy)-ethoxy]-ethoxy}-ethylcarbamoyl)-2-methoxy-phenyl]-amide, dimer, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(2-{2-[2-(2-amino-ethoxy)-ethoxy]-ethoxy}-ethylcarbamoyl)-2-methoxy-phenyl]-amide, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid ((S)-1-allyloxycarbonyl-5-tert-butoxycarbonylamino-pentylcarbamoyl)-methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-1000 amide, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-1000 ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-2000 amide and 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-2000 ester.

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, CF$_3$, NH$_2$, N(H, lower-alkyl), N(lower-alkyl)$_2$, aminocarbonyl, carboxy, NO$_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, NH$_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, NH$_2$, N(H, lower-alkyl) or N(lower-alkyl)$_2$. Preferred substituents for the cycloalkyl, cycloalkenyl, aryl, heteroaryl and heterocycle rings are halogen, lower alkoxy, lower alkyl, hydroxycarbonyl, carboxy, carboxy lower alkoxy, oxo and CN. Preferred substituents for alkyl are alkoxy and N(lower alkyl)$_2$.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl. Where the aryl group is bicyclic a preferred group is 1,3-dioxo-2,3-dihydro-1H-isoindol-5-yl group.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole substituted or unsubstituted triazolyl and substituted or unsubstituted tetrazolyl.

In the case of aryl or heteroaryl which are bicyclic it should be understood that one ring may be aryl while the other is heteroaryl and both being substituted or unsubstituted.

"Heterocycle" or "heterocyclic ring" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like which in turn can be substituted. "Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formula I as well as their salts that have at least one asymmetric carbon atom may be present as racemic mixtures or different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

The compounds of the present invention are useful in the treatment or control of cell proliferative disorders, in particular oncological disorders. These compounds and formulations containing said compounds may be particularly useful in the treatment or control of solid tumors, such as, for example, breast, colon, lung and prostate tumors. The compounds may also be useful in the treatment of certain non-solid tumors such as leukemia's and lymphoma's.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration; it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit MDM2 interaction with p53. For example, such amount may be below the amount that is toxic to normal cells, or the mammal as a whole.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

"Effective amount" means an amount that is effective to prevent, alleviate or ameliorate symptoms of disease or prolong the survival of the subject being treated.

"IC50" refers to the concentration of a particular compound required to inhibit 50% of a specific measured activity. $IC_{50}$ can be measured, inter alia, as is described subsequently.

Synthetic Methods

The general method for the preparation of compounds of formula I is given in Scheme 1. Briefly, the process involves coupling of R₃—NH₂ or R₃—OH with the benzoic acid II using the typical conditions known in the art.

Scheme 1

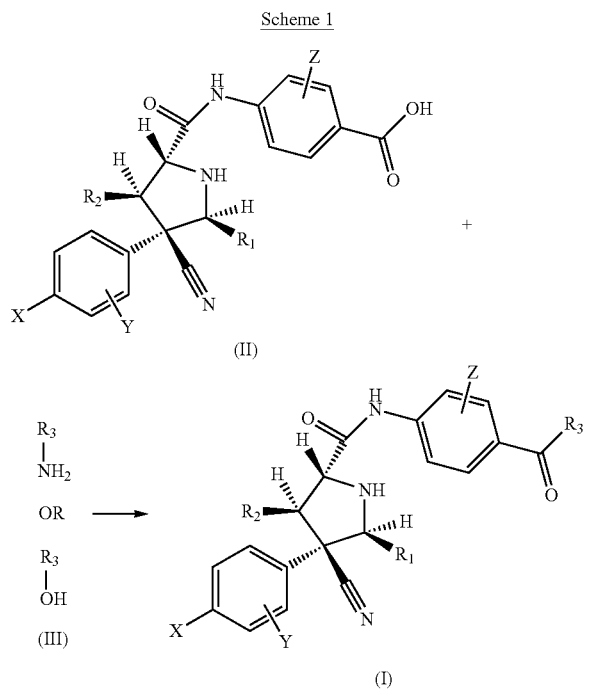

The following examples and references are provided to aid the understanding of the present invention. However, the true scope of the invention is set forth in the appended claims.

Example 1

2-Hydroxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

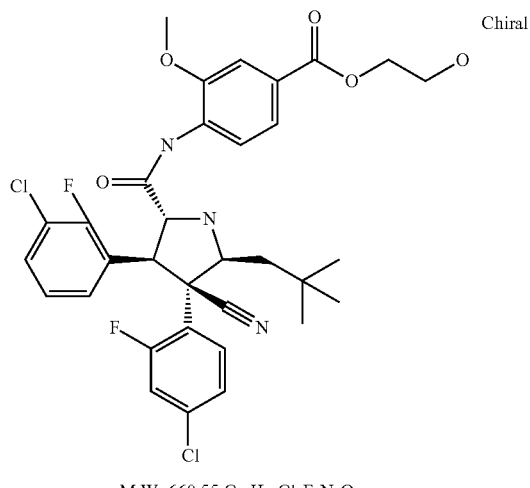

M.W. 660.55 $C_{33}H_{33}Cl_2F_2N_3O_5$

To a suspension of chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (US20100152190A1, 197 mg, 0.320 mmol,) in methylene chloride (8 mL) was added triethylamine (97.0 mg, 0.14 mL, 0.959 mmol) followed by bis(2-oxo-3-oxazolidinyl)phosphinic chloride (Aldrich, 114 mg, 0.447 mmol). The mixture was stirred at room temperature for 10 min before ethane-1,2-diol (Aldrich, 122 mg, 0.11 mL, 1.97 mmol) was added. This reaction mixture was stirred at room temperature overnight. It was then diluted with methylene chloride and washed with water, brine and concentrated to dryness. The crude material was purified by flash chromatography (eluting with hexane/ethyl acetate, 80/20 to 10/90) to give chiral 2-hydroxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white solid (112.2 mg, 53% yield). MS (ES⁺) m/z calcd. for $C_{33}H_{34}Cl_2F_2N_3O_5$ [(M+H)⁺]: 660. found: 660.

Example 2

2-(2-Hydroxyethoxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

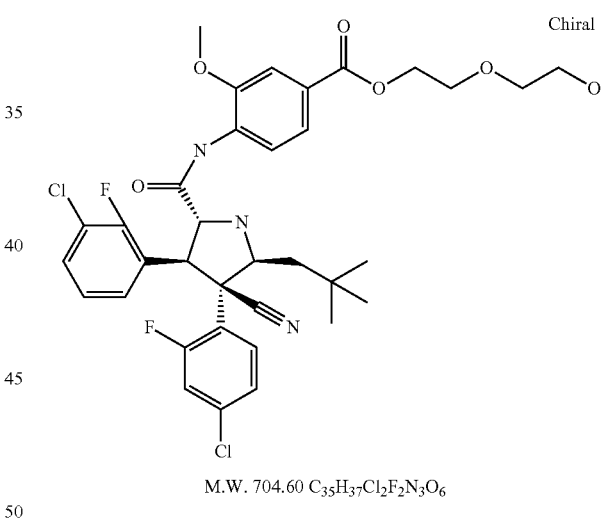

M.W. 704.60 $C_{35}H_{37}Cl_2F_2N_3O_6$

To a suspension of chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (150 mg, 0.243 mmol) in methylene chloride (8 mL) was added triethylamine (72.0 mg, 0.10 mL, 0.717 mmol) followed by bis(2-oxo-3-oxazolidinyl)phosphinic chloride (Aldrich, 92 mg, 0.365 mmol). The mixture was stirred at room temperature for 10 min before 2,2'-oxydiethanol (Aldrich, 154 mg, 0.14 mL, 1.45 mmol) was added. This reaction mixture was stirred at room temperature overnight. It was then diluted with methylene chloride and washed with water, brine and concentrated to dryness. The crude material was purified by flash chromatography (eluting with hexane/ethyl acetate, 80/20 to 10/90) to give chiral 2-(2-hydroxyethoxy)ethyl 4-((2R,3S,4R,5S)-3-(3-chloro-2-fluorophenyl)-4-(4-chloro-2-fluorophenyl)-4-cyano-5-neopentylpyrrolidine-2- carboxamido)-3-methoxybenzoate as a white solid (40.8 mg, 23% yield). MS (ES+) m/z calcd. for $C_{35}H_{38}Cl_2F_2N_3O_6$ [(M+H)+]: 704. found: 704.

Example 3

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 2-((S)-2-tert-butoxycarbonylamino-propionyloxy)-ethyl ester

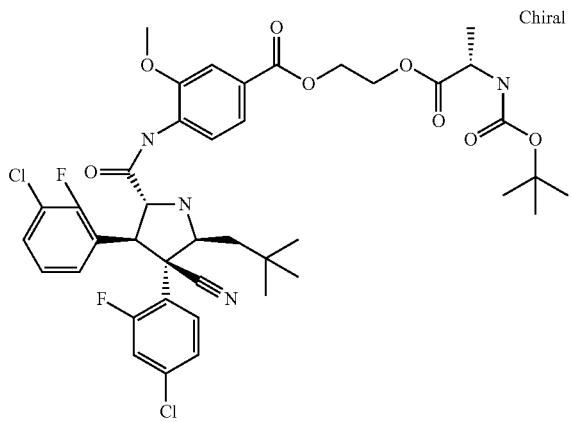

M.W. 831.75 $C_{41}H_{46}Cl_2F_2N_4O_8$

A mixture of (S)-L-(2-(tert-butoxycarbonylamino)propanoic acid (Chem-Impex, 13.6 mg, 0.072 mmol), HATU (Bachem, 27.3 mg, 0.072 mmol), N,N-diisopropylethylamine (18.6 mg, 0.025 mL, 0.144 mmol) and dimethylaminopyridine (Aldrich, 2.2 mg, 0.018 mmol) in dimethyl formamide (8 mL) was stirred for 10 min before 2-hydroxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (Example 1, 19 mg, 0.028 mmol) in dimethyl formamide (1 mL) was added. The reaction mixture was stirred overnight and then diluted with ethyl acetate, washed successively with aqueous sodium bicarbonate solution, water (3×15 mL) and brine (15 mL), dried over anhydrous sodium sulfate and concentrated. The crude material was purified by flash chromatography (hexane/ethyl acetate, 95/5 to 65/35) to give chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 2-((S)-2-tert-butoxycarbonylamino-propionyloxy)-ethyl ester as a white solid (17 mg, 71% yield). MS (ES+) m/z calcd. for $C_{41}H_{47}Cl_2F_2N_4O_8$ [(M+H)+]: 831. found: 831.

Example 4

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 2-((S)-2-amino-propionyloxy)-ethyl ester

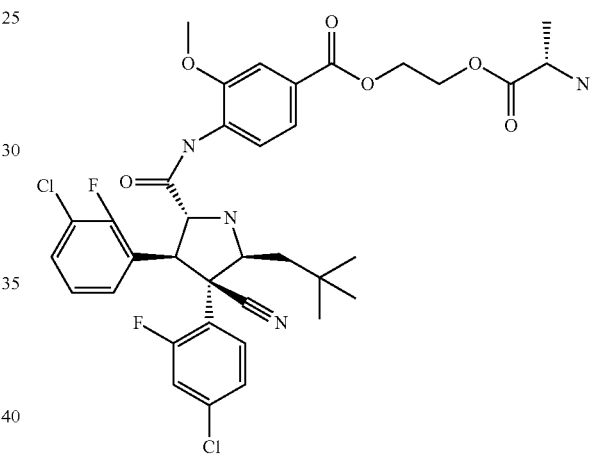

M.W. 731.63 $C_{36}H_{38}Cl_2F_2N_4O_6$

To a solution of chiral 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 2-((S)-2-tert-butoxycarbonylamino-propionyloxy)-ethyl ester (Example 3, 98.2 mg, 0.118 mmol) in methylene chloride (4 mL) at 0° C. was added trifluoroacetic acid (2 mL) slowly and the mixture was allowed to stir at 0° C. for 1 h. The mixture was concentrated and the residue was taken up in methylene chloride (100 mL), washed successively with aqueous sodium carbonate and water and concentrated. The material was treated with acetonitrile and water and lyophilized to give chiral 4-{[(2R,3S,4R,5S)-3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 2-((S)-2-aminopropionyloxy)-ethyl ester as a white solid (78 mg, 90% yield). MS (ES+) m/z calcd. for $C_{36}H_{39}Cl_2F_2N_4O_6$ [(M+H)+]: 731. found: 731.

Example 5

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 2-((R)-2-tert-butoxycarbonylamino-propionyloxy)-ethyl ester

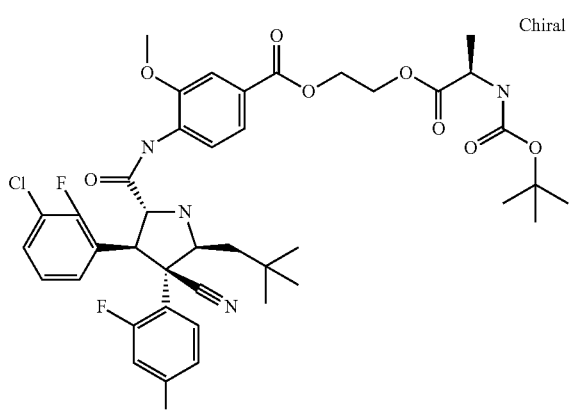

M.W. 831.75 $C_{41}H_{46}Cl_2F_2N_4O_8$ $C_{41}H_{47}Cl_2F_2N_4O_8$ [(M+H)+]: 831. found: 831.

Example 6

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 2-((R)-2-amino-propionyloxy)-ethyl ester

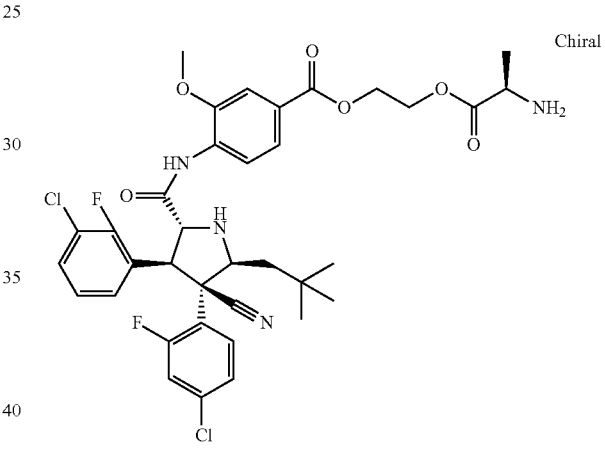

M.W. 731.63 $C_{36}H_{38}Cl_2F_2N_4O_6$

In a manner similar to the method described in Example 3, chiral 2-hydroxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (Example 1, 105.2 mg, 0.159 mmol) was reacted with (R)-(2-(tert-butoxycarbonylamino)propanoic acid (Chem-Impex, 75 mg, 0.398 mmol), HATU (Bachem, 151 mg, 0398 mmol), N,N-diisopropylethylamine (104 mg, 0.14 mL, 0.802 mmol) and dimethylaminopyridine (Aldrich, 10.8 mg, 0.088 mmol) in dimethyl formamide (8 mL) to give chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 2-((R)-2-tert-butoxycarbonylamino-propionyloxy)-ethyl ester as a white solid (119 mg, 89% yield). MS (ES+) m/z calcd. for In a manner similar to the method described in Example 4, chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 2-((R)-2-tert-butoxycarbonylamino-propionyloxy)-ethyl ester (Example 5, 112 mg, 0.135 mmol) in methylene chloride (2 mL) was treated with trifluoroacetic acid (2 mL) to give chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 2-((R)-2-amino-propionyloxy)-ethyl ester as a white solid. MS (ES+) m/z calcd. for $C_{36}H_{39}Cl_2F_2N_4O_6$ [(M+H)+]: 731. found: 731.

Example 7

2-(Dimethylamino)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

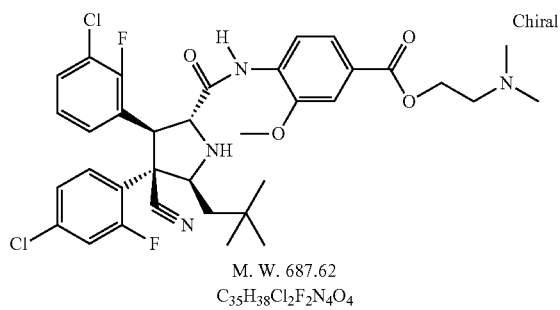 [SMILES: COc1cc(C(=O)OCCN(C)C)ccc1NC(=O)[C@@H]1N[C@@H](CC(C)(C)C)[C@](C#N)(c2ccc(Cl)cc2F)[C@H]1c1cccc(Cl)c1F]

M. W. 687.62
$C_{35}H_{38}Cl_2F_2N_4O_4$

A mixture of chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (100.2 mg, 0.164 mmol) and N,N'-carbonyldiimidazole (68.8 mg, 0.424 mmol, Aldrich) in tetrahydrofuran (5 mL) was stirred at room temperature overnight. N,N-dimethylethanolamine (44.3 mg, 0.495 mmol, Aldrich) was added to a suspension of sodium hydride (12 mg, 0.475 mmol) in tetrahydrofuran (4 mL) and stirred at room temperature for 1 h. It was then added to the above mixture and stirred at room temperature for 1 h. The reaction mixture was quenched with water and extracted with ethyl acetate. The organic layer was washed with water, brine and dried over anhydrous sodium sulfate and concentrated. the crude product was purified by flash chromatography to give chiral 2-(dimethylamino)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white solid (97.2 mg, 86% yield). MS (ES$^+$) m/z calcd. for $C_{35}H_{39}Cl_2F_2N_4O_4$ [(M+H)$^+$]: 687. found: 687.

Example 8

(2,2-Dimethyl-1,3-dioxolan-4-yl)methyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

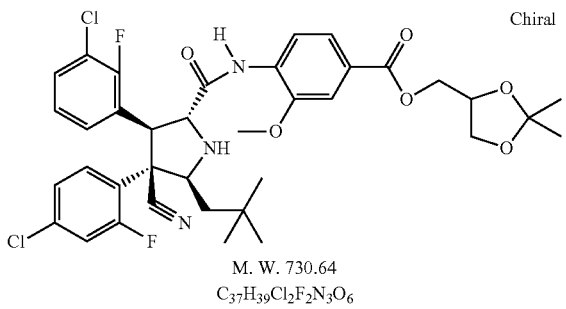 [SMILES: COc1cc(C(=O)OCC2COC(C)(C)O2)ccc1NC(=O)[C@@H]1N[C@@H](CC(C)(C)C)[C@](C#N)(c2ccc(Cl)cc2F)[C@H]1c1cccc(Cl)c1F]

M. W. 730.64
$C_{37}H_{39}Cl_2F_2N_3O_6$

In a manner similar to the method described in Example 7, chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (100.8 mg, 0.164 mmol) was reacted with N,N'-carbonyldiimidazole (Aldrich, 67.8 mg, 0.406 mmol) and then a mixture of (2,2-Dimethyl-[1,3]dioxolan-4-yl)-methanol (Aldrich, 69.3 mg, 0.514 nmol) and sodium hydride (11.2 mg, 0.443 mmol) in tetrahydrofuran to give (2,2-dimethyl-1,3-dioxolan-4-yl)methyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white lyophilized solid (104.2 mg, 87% yield). MS (ES$^+$) m/z calcd. for $C_{37}H_{40}Cl_2F_2N_3O_6$ [(M+H)$^+$]: 730. found: 730.

Example 9

3-Hydroxy-2-(hydroxymethyl)propyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

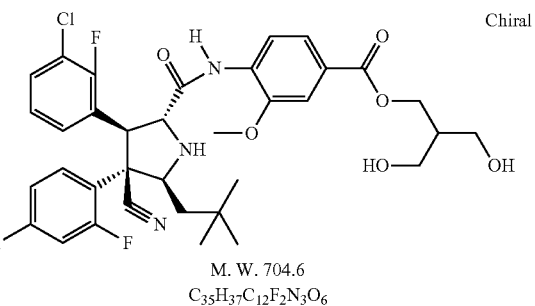

M. W. 704.6
$C_{35}H_{37}Cl_2F_2N_3O_6$

In a manner similar to the method described in Example 7, chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (100.2 mg, 0.163 mmol) was reacted with N,N'-carbonyldiimidazole (Aldrich, 69.5 mg, 0.416 mmol) and then, a mixture of 2-(hydroxymethyl)-1,3-propanediol (Aldrich, 91.8 mg, 0.839 mmol) and sodium hydride (41.6 mg, 1.65 mmol) in tetrahydrofuran to give chiral 3-hydroxy-2-(hydroxymethyl)propyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white lyophilized solid (57.5 mg, 50% yield). MS (ES$^+$) m/z calcd. for $C_{35}H_{38}Cl_2F_2N_3O_6$: [(M+H)$^+$]: 704. found: 704.

Example 10

2-Methoxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

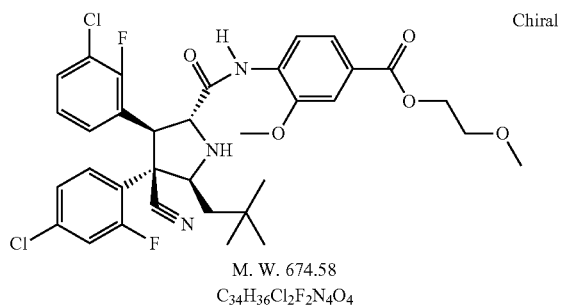 [SMILES: COCCOC(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]

M. W. 674.58
C$_{34}$H$_{36}$Cl$_2$F$_2$N$_4$O$_4$

In a manner similar to the method described in Example 7, chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (100.4 mg, 0.163 mmol) was reacted with N,N'-carbonyldiimidazole (Aldrich, 69.2 mg, 0.414 mmol) and then, a mixture of 2-methoxyethanol (Sigma Aldrich, 38.6 mg, 0.506 mmol) and sodium hydride (9.7 mg, 0.384 mmol) in tetrahydrofuran to give chiral 2-methoxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white solid (89 mg, 81% yield). MS (ES$^+$) m/z calcd. for C$_{34}$H$_{37}$Cl$_2$F$_2$N$_4$O$_4$ [(M+H)$^+$]: 674. found: 674.

Example 11

2-Iodoethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

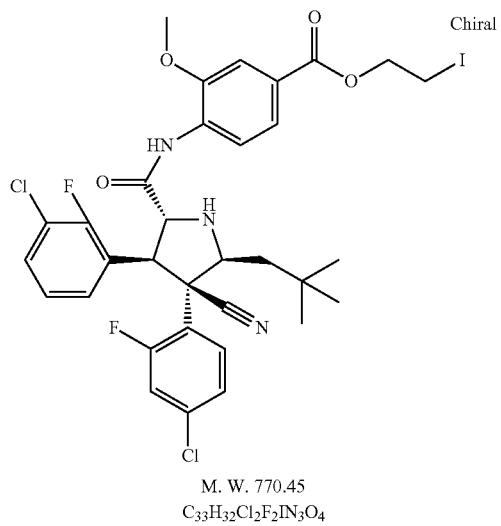 [SMILES: COc1cc(C(=O)OCCI)ccc1NC(=O)[C@@H]1N[C@@H](CC(C)(C)C)[C@](C#N)(c2ccc(Cl)cc2F)[C@H]1c1cccc(Cl)c1F]

M. W. 770.45
C$_{33}$H$_{32}$Cl$_2$F$_2$IN$_3$O$_4$

In a manner similar to the method described in Example 1, chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (200 mg, 0.324 mmol) was reacted with iodoethanol (Aldrich, 220 mg, 1.28 mmol) in the presence of bis(2-oxo-3-oxazolidinyl)phosphinic chloride (Aldrich, 121.6 mg, 0.478 mmol), triethylamine (203 mg, 2.00 mmol) to give chiral 2-iodoethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as an off-white solid (137.4 mg, 55% yield). MS (ES$^+$) m/z calcd. for C$_{33}$H$_{33}$Cl$_2$F$_2$IN$_3$O$_4$: [(M+H)$^+$]: 770. found: 770.

Example 12

2-(Di-tert-butoxyphosphoryloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

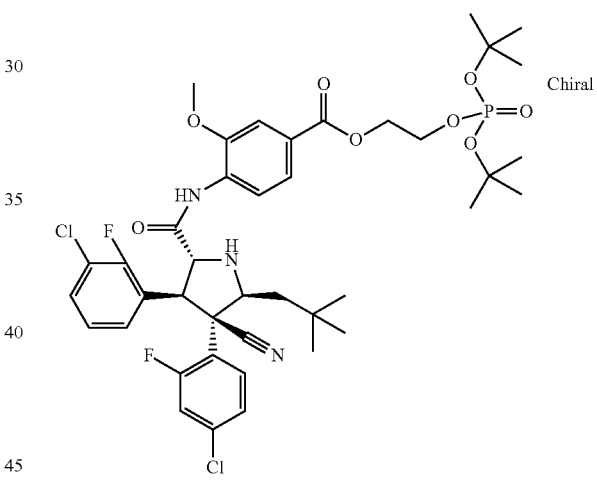

M. W. 852.75
C$_{41}$H$_{50}$Cl$_2$F$_2$N$_3$O$_8$P

To a solution of chiral 2-iodoethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (Example 11, 20 mg, 0.026 mmol) in dimethyl formamide (2 mL) was added potassium di-tert-butylphosphate (Accela ChemBio, 21.8 mg, 0.088 mmol). The reaction mixture was heated at 60° C. for 6 h. The mixture was diluted with ethyl acetate, washed with water and then brine, dried over anhydrous sodium sulfate and concentrated. The crude material was purified by flash chromatography to give chiral 2-(di-tert-butoxyphosphoryloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (12 mg, 54% yield). MS (ES$^+$) m/z calcd. for C$_{41}$H$_{50}$Cl$_2$F$_2$N$_3$O$_8$PNa: [(M+Na)$^+$]: 874. found: 874.

Example 13

2-(Phosphonooxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, trifluoroacetate salt

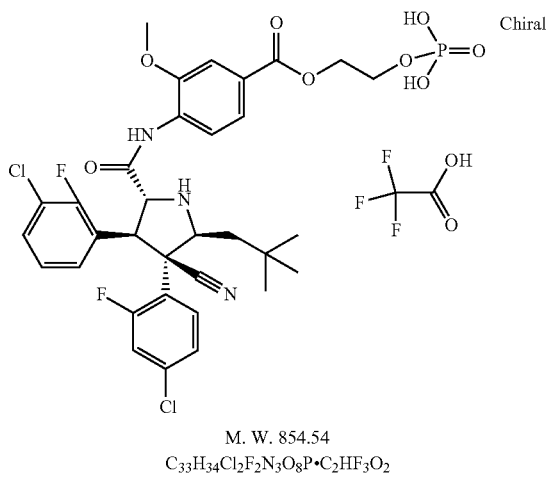 [SMILES: COc1cc(C(=O)OCCOP(=O)(O)O)ccc1NC(=O)[C@@H]1N[C@@H](CC(C)(C)C)[C@](C#N)(c2ccc(Cl)cc2F)[C@H]1c1cccc(Cl)c1F ; O=C(O)C(F)(F)F]

M. W. 854.54
$C_{33}H_{34}Cl_2F_2N_3O_8P \cdot C_2HF_3O_2$

A solution of chiral 2-(di-tert-butoxyphosphoryloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (Example 12, 89.1 mg, 0.104 mmol) in methylene chloride (2 mL) was treated with trifluoroacetic acid (1 mL) and stirred for 45 min at 0° C. The reaction mixture was concentrated and the product was lyophilized to give chiral 2-(phosphonooxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate trifluoroacetate as a white solid (80.7 mg, 90% yield). MS (ES$^+$) m/z calcd. for $C_{33}H_{35}Cl_2F_2N_3O_8P$: [(M+H)$^+$]: 740. found: 740.

Example 14

Rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(2-hydroxy-1-methyl-ethylcarbamoyl)-2-methoxy-phenyl]-amide

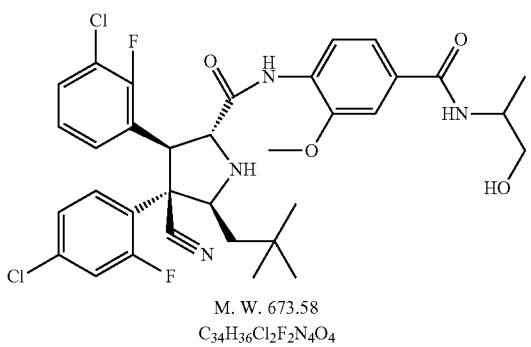 [SMILES: COc1cc(C(=O)NC(C)CO)ccc1NC(=O)[C@@H]1N[C@@H](CC(C)(C)C)[C@](C#N)(c2ccc(Cl)cc2F)[C@H]1c1cccc(Cl)c1F]

M. W. 673.58
$C_{34}H_{36}Cl_2F_2N_4O_4$ 4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1, 119.9 mg, 194 µmol) was suspended in methylene chloride (5 mL), then N,N-diisopropylethylamine (156 mg, 210 µL, 1.21 mmol) was added, followed by (2-(7-aza-1H-benzotriazole-1-yl)-1,1,3,3-tetramethyluronium hexafluorophosphate) (HATU, 120 mg, 316 µmol). After stirring at room temperature under argon for a few minutes, DL-alaminol (24.1 mg, 25 µL, 321 µmol) was added. The reaction progress was monitored by LC-MS. After its completion (~2 h), the reaction mixture was taken in ethyl acetate (75 mL) and water (15 mL). The layers were separated, and the organic layers were washed with saturated solution of sodium bicarbonate (10 mL), water (15 mL), brine (15 mL), and dried over anhydrous sodium sulfate. The solids were filtered off, and the crude residue was purified by flash chromatography (8 g of silica gel, eluting with 0.5-5.0% ethanol in methylene chloride) to give rac-(2R,3S,4R,5S)-3-(3-chloro-2-fluorophenyl)-4-(4-chloro-2-fluorophenyl)-4-cyano-N-(4-(1-hydroxypropan-2-ylcarbamoyl)-2-methoxyphenyl)-5-neopentylpyrrolidine-2-carboxamide (118.9 mg, 177 µmol, 90.8% yield) as white solids. MS (ES$^+$) m/z calcd. for $C_{34}H_{37}Cl_2F_2N_4O_4$: [(M+H)$^+$]: 673. found: 673.

Example 16

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-diethylamino-ethyl ester

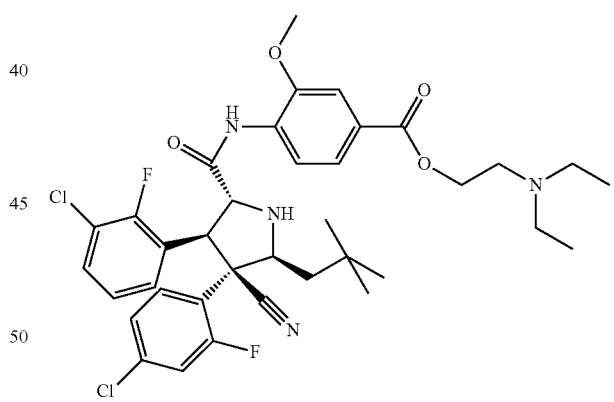

M. W. 715.66
$C_{37}H_{42}Cl_2F_2N_4O_4$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 2-(diethylamino)ethanol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-diethylamino-ethyl ester. MS (ES$^+$) m/z calcd. for $C_{37}H_{43}Cl_2F_2N_4O_4$: [(M+H)$^+$]: 715. found: 715.

Example 17

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-methyl-piperidin-4-yl ester

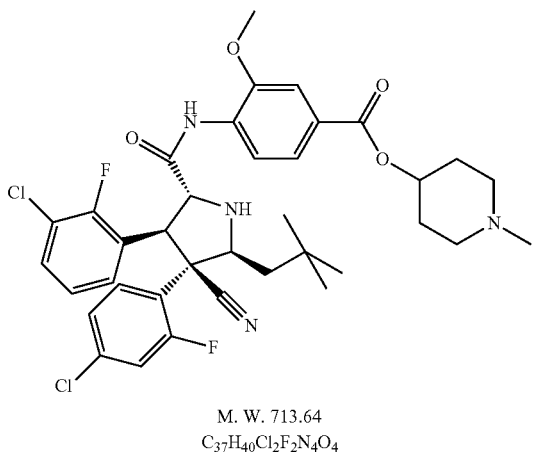 [SMILES: COc1cc(C(=O)OC2CCN(C)CC2)ccc1NC(=O)[C@@H]1N[C@@H](CC(C)(C)C)[C@](C#N)(c2ccc(Cl)cc2F)[C@H]1c1cccc(Cl)c1F]

M. W. 713.64
$C_{37}H_{40}Cl_2F_2N_4O_4$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 1-methylpiperidin-4-ol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-methyl-piperidin-4-yl ester. MS (ES$^+$) m/z calcd. for $C_{37}H_{41}Cl_2F_2N_4O_4$: [(M+H)$^+$]: 713. found: 713.

Example 18

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-methyl-piperidin-4-ylmethyl ester

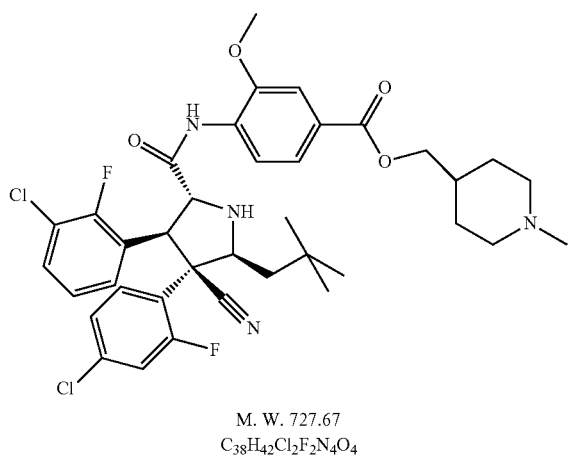 [SMILES: COc1cc(C(=O)OCC2CCN(C)CC2)ccc1NC(=O)[C@@H]1N[C@@H](CC(C)(C)C)[C@](C#N)(c2ccc(Cl)cc2F)[C@H]1c1cccc(Cl)c1F]

M. W. 727.67
$C_{38}H_{42}Cl_2F_2N_4O_4$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with (1-methylpiperidin-4-yl)methanol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-methyl-piperidin-4-ylmethyl ester. MS (ES$^+$) m/z calcd. for $C_{38}H_{43}Cl_2F_2N_4O_4$: [(M+H)$^+$]: 727. found: 727.

Example 19

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(4-methyl-piperazin-1-yl)-ethyl ester

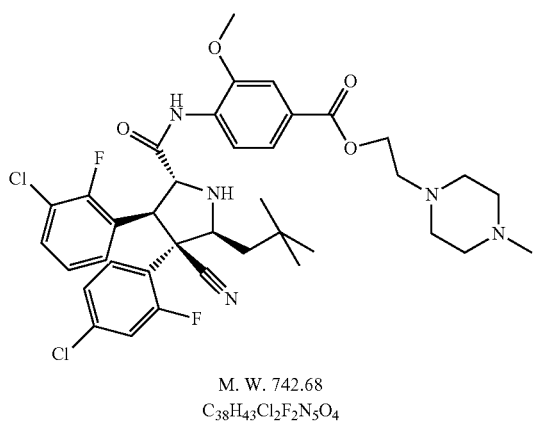 [SMILES: COc1cc(C(=O)OCCN2CCN(C)CC2)ccc1NC(=O)[C@@H]1N[C@@H](CC(C)(C)C)[C@](C#N)(c2ccc(Cl)cc2F)[C@H]1c1cccc(Cl)c1F]

M. W. 742.68
$C_{38}H_{43}Cl_2F_2N_5O_4$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 2-(4-methylpiperazin-1-yl)ethanol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(4-methyl-piperazin-1-yl)-ethyl ester. MS (ES$^+$) m/z calcd. for $C_{38}H_{44}Cl_2F_2N_5O_4$: [(M+H)$^+$]: 742. found: 742.

Example 20

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid [1,2,3]triazolo[4,5-b]pyridin-3-yl ester

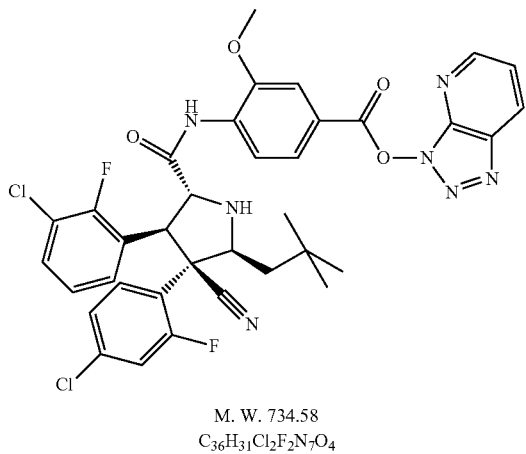 [SMILES: COc1cc(C(=O)On2nnc3cccnc32)ccc1NC(=O)[C@@H]1N[C@@H](CC(C)(C)C)[C@](C#N)(c2ccc(Cl)cc2F)[C@H]1c1cccc(Cl)c1F]

M. W. 734.58
$C_{36}H_{31}Cl_2F_2N_7O_4$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with HATU to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid [1,2,3]triazolo[4,5-b]pyridin-3-yl ester. MS (ES+) m/z calcd. for $C_{36}H_{32}Cl_2F_2N_7O_4$: $[(M+H)^+]$: 734. found: 734.

Example 21

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-methyl-2-morpholin-4-yl-ethyl ester

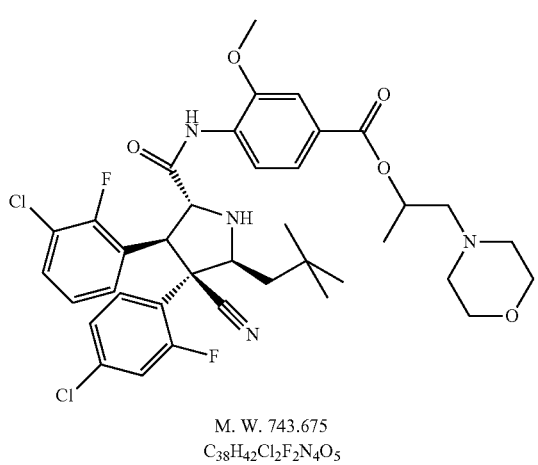 [SMILES: COc1cc(C(=O)OC(C)CN2CCOCC2)ccc1NC(=O)[C@@H]1N[C@@H](CC(C)(C)C)[C@](C#N)(c2ccc(Cl)cc2F)[C@H]1c1cccc(Cl)c1F]

M. W. 743.675
$C_{38}H_{42}Cl_2F_2N_4O_5$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 1-morpholinopropan-2-ol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-methyl-2-morpholin-4-yl-ethyl ester. MS (ES+) m/z calcd. for $C_{38}H_{43}Cl_2F_2N_4O_5$: $[(M+H)^+]$: 743. found: 743.

Example 22

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-morpholin-4-yl-ethyl ester

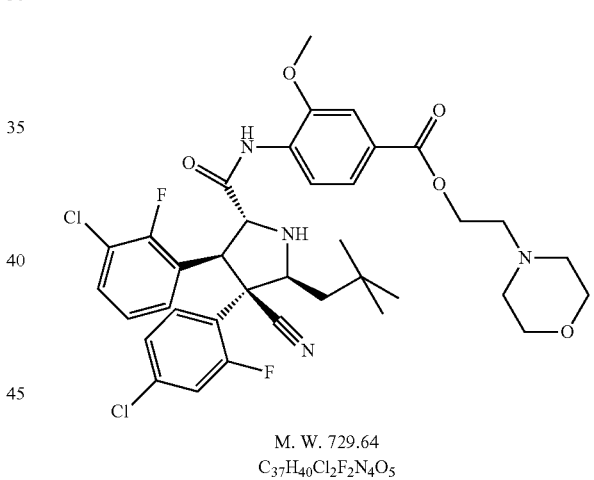

M. W. 729.64
$C_{37}H_{40}Cl_2F_2N_4O_5$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 2-morpholinoethanol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-morpholin-4-yl-ethyl ester. MS (ES+) m/z calcd. for $C_{37}H_{41}Cl_2F_2N_4O_5$: $[(M+H)^+]$: 729. found: 729.

Example 23

(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(2-diethylamino-ethylcarbamoyl)-2-methoxy-phenyl]-amide, hydrochloride

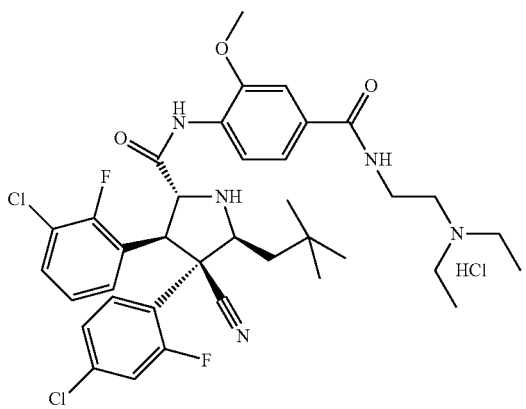

M.W. 787.59
$C_{37}H_{43}Cl_2F_2N_5O_3 \cdot 2HCl$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with N,N-diethylethane-1,2-diamine to give (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid [4-(2-diethylamino-ethylcarbamoyl)-2-methoxy-phenyl]-amide hydrochloride. MS (ES+) m/z calcd. for $C_{37}H_{44}Cl_2F_2N_5O_3$: [(M+H)+]: 714. found: 714.

Example 24

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid dimethylcarbamoylmethyl ester, hydrochloride

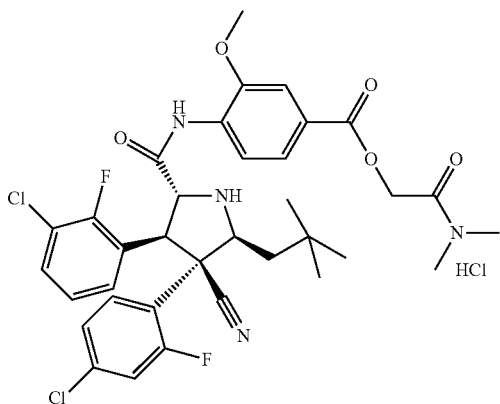

M.W. 774.51
$C_{35}H_{36}Cl_2F_2N_4O_5 \cdot 2HCl$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 2-hydroxy-N,N-dimethylacetamide to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid dimethylcarbamoylmethyl ester, hydrochloride. MS (ES+) m/z calcd. for $C_{35}H_{37}Cl_2F_2N_4O_5$: [(M+H)+]: 703. found: 703.

Example 25

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-morpholin-4-yl-propyl ester, hydrochloride

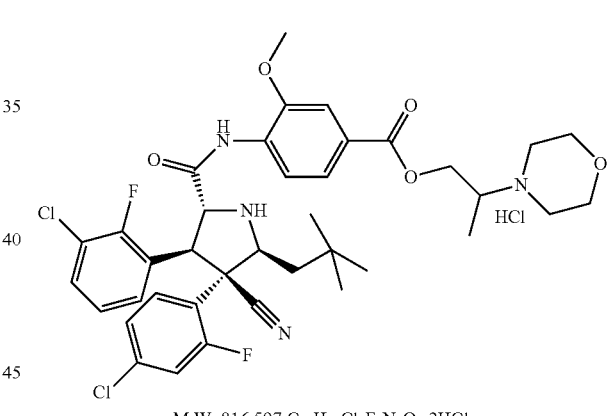

M.W. 816.597 $C_{38}H_{42}Cl_2F_2N_4O_5 \cdot 2HCl$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 2-morpholinopropan-1-ol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-morpholin-4-yl-propyl ester, hydrochloride. MS (ES+) m/z calcd. for $C_{38}H_{43}Cl_2F_2N_4O_5$: [(M+H)+]: 744. found: 744.

Example 26

(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid {2-methoxy-4-[2-(4-methyl-piperazin-1-yl)-ethylcarbamoyl]-phenyl}-amide, hydrochloride

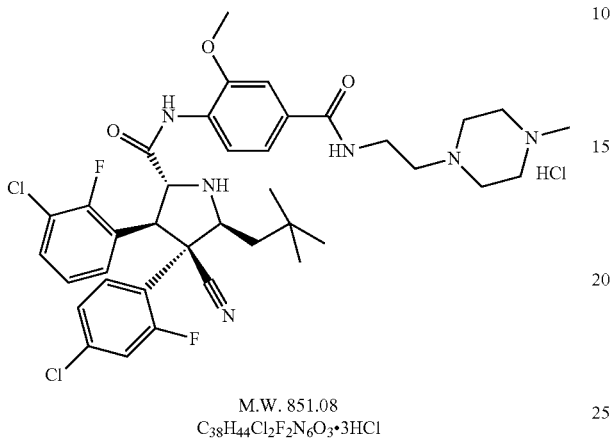

M.W. 851.08
$C_{38}H_{44}Cl_2F_2N_6O_3 \cdot 3HCl$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 2-(4-methylpiperazin-1-yl)ethanamine to give (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid {2-methoxy-4-[2-(4-methyl-piperazin-1-yl)-ethylcarbamoyl]-phenyl}-amide, hydrochloride. MS (ES$^+$) m/z calcd. for $C_{38}H_{45}Cl_2F_2N_6O_3$: [(M+H)$^+$]: 741. found: 741.

Example 27

(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethyl-carbamoyl-2-methoxy-phenyl)-amide

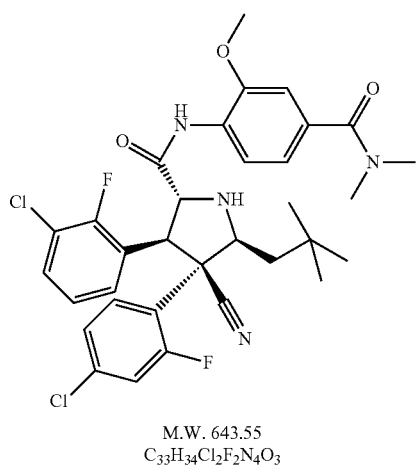 [SMILES: COc1cc(C(=O)N(C)C)ccc1NC(=O)[C@@H]1N[C@@H](CC(C)(C)C)[C@](C#N)(c2ccc(Cl)cc2F)[C@H]1c1cccc(Cl)c1F]

M.W. 643.55
$C_{33}H_{34}Cl_2F_2N_4O_3$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with dimethylamine to give (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-dimethylcarbamoyl-2-methoxy-phenyl)-amide. MS (ES$^+$) m/z calcd. for $C_{33}H_{35}Cl_2F_2N_4O_3$: [(M+H)$^+$]: 643. found: 643.

Example 28

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (2S,3R,4R,5R)-2,3,4,5,6-pentahydroxy-hexyl ester

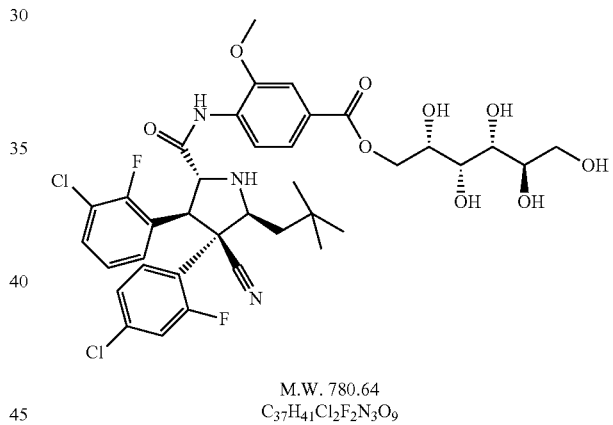

M.W. 780.64
$C_{37}H_{41}Cl_2F_2N_3O_9$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with (2R,3R,4R,5S)-hexane-1,2,3,4,5,6-hexaol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (2S,3R,4R,5R)-2,3,4,5,6-pentahydroxy-hexyl ester. MS (ES$^+$) m/z calcd. for $C_{37}H_{42}Cl_2F_2N_3O_9$: [(M+H)$^+$]: 780. found: 780.

Example 29

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-tert-butoxycarbonylamino-acetoxy)-ethyl ester

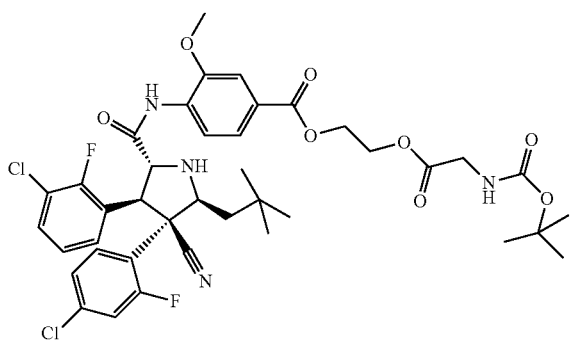

M.W. 817.7
$C_{40}H_{44}Cl_2F_2N_4O_8$

In a manner similar to the method described in Example 3, 2-hydroxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate was reacted with 2-(tert-butoxycarbonylamino)acetic acid to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-tert-butoxycarbonylamino-acetoxy)-ethyl ester. MS (ES$^+$) m/z calcd. for $C_{40}H_{45}Cl_2F_2N_4O_8$: [(M+H)$^+$]: 817. found: 817.

Example 30

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-amino-acetoxy)-ethyl ester

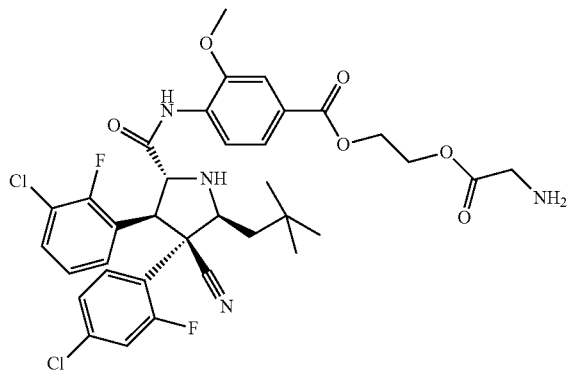

M.W. 717.593
$C_{35}H_{36}Cl_2F_2N_4O_6$

4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-tert-butoxycarbonylamino-acetoxy)-ethyl ester (Example 29) was treated with trifluoroacetic acid to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-amino-acetoxy)-ethyl ester. MS (ES$^+$) m/z calcd. for $C_{35}H_{37}Cl_2F_2N_4O_6$: [(M+H)$^+$]: 717. found: 717.

Example 31

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(tert-butoxycarbonyl-methyl-amino)-acetoxy]-ethyl ester

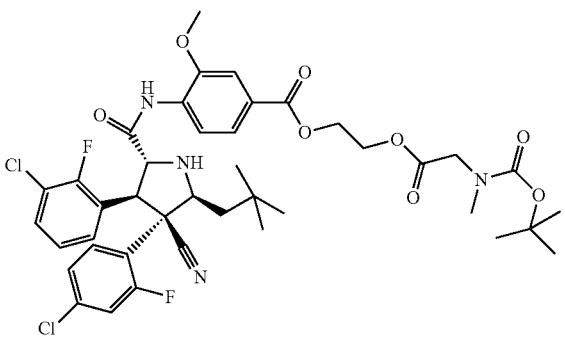

M.W. 831.73
$C_{41}H_{46}Cl_2F_2N_4O_8$

In a manner similar to the method described in Example 3, 2-hydroxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate was reacted with 2-(tert-butoxycarbonyl(methyl)amino)-acetic acid to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(tert-butoxycarbonyl-methyl-amino)-acetoxy]-ethyl ester. MS (ES$^+$) m/z calcd. for $C_{41}H_{47}Cl_2F_2N_4O_8$: [(M+H)$^+$]: 831. found: 831.

Example 32

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-methylamino-acetoxy)-ethyl ester, hydrochloride

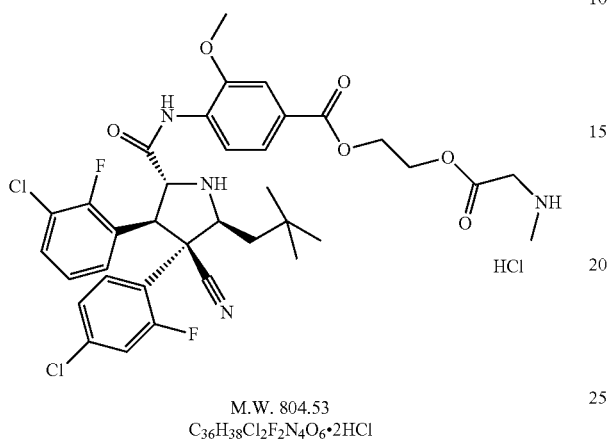

M.W. 804.53
$C_{36}H_{38}Cl_2F_2N_4O_6 \cdot 2HCl$

4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(tert-butoxycarbonyl-methyl-amino)-acetoxy]-ethyl ester (Example 31) was treated with trifluoroacetic acid to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-methylamino-acetoxy)-ethyl ester, hydrochloride. MS (ES$^+$) m/z calcd. for $C_{36}H_{39}Cl_2F_2N_4O_6$: [(M+H)$^+$]: 731. found: 731.

Example 33

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[(S)-3-methyl-2-((S)-2-tert-butoxycarbonyl-methylamino-propionylamino)-butyryloxy]-ethyl ester

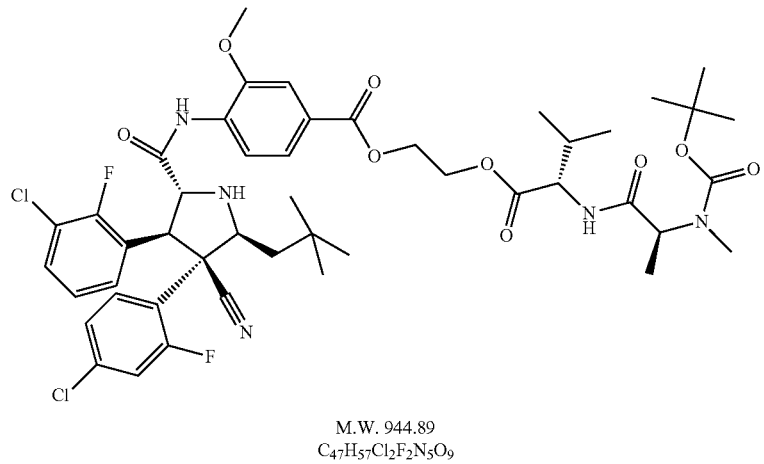 [SMILES: COc1cc(C(=O)OCCOC(=O)[C@@H](NC(=O)[C@H](C)N(C)C(=O)OC(C)(C)C)C(C)C)ccc1NC(=O)[C@@H]1N[C@@H](CC(C)(C)C)[C@](C#N)(c2ccc(Cl)cc2F)[C@H]1c1cccc(Cl)c1F]

M.W. 944.89
$C_{47}H_{57}Cl_2F_2N_5O_9$

In a manner similar to the method described in Example 3, 2-hydroxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (Example 1) was reacted with (S)-2-((S)-2-(tert-butoxycarbonyl(methyl)amino)propanamido)-3-methylbutanoic acid to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[(S)-3-methyl-2-((S)-2-tert-butoxycarbonyl-methylamino-propionylamino)-butyryloxy]-ethyl ester. MS (ES$^+$) m/z calcd. for $C_{47}H_{58}Cl_2F_2N_5O_9$: [(M+H)$^+$]: 944. found: 944.

Example 34

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[(S)-3-methyl-2-((S)-2-methylamino-propionylamino)-butyryloxy]-ethyl ester, hydrochloride

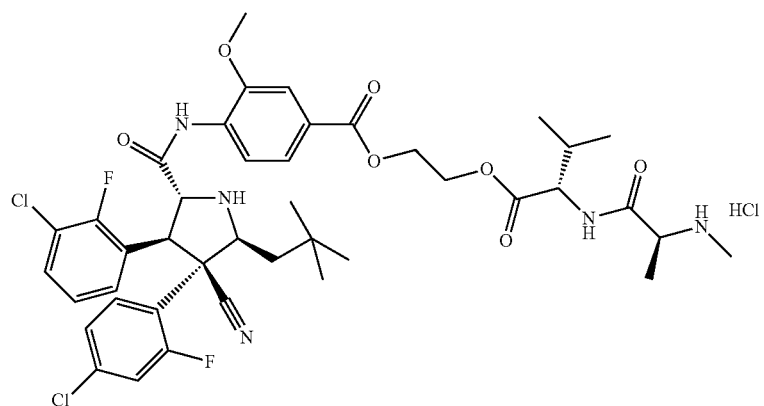

M.W. 917.69
$C_{42}H_{49}Cl_2F_2N_5O_7 \cdot 2HCl$

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[(S)-3-methyl-2-((S)-2-tert-butoxycarbonyl-methylamino-propionylamino)-butyryloxy]-ethyl ester (Example 33) was reacted with trifluoroacetic acid to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[(S)-3-methyl-2-((S)-2-methylamino-propionylamino)-butyryloxy]-ethyl ester, hydrochloride. MS (ES$^+$) m/z calcd. for $C_{42}H_{50}Cl_2F_2N_5O_7$: [(M+H)$^+$]: 844. found: 844.

Example 35

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid methoxycarbonylmethyl ester

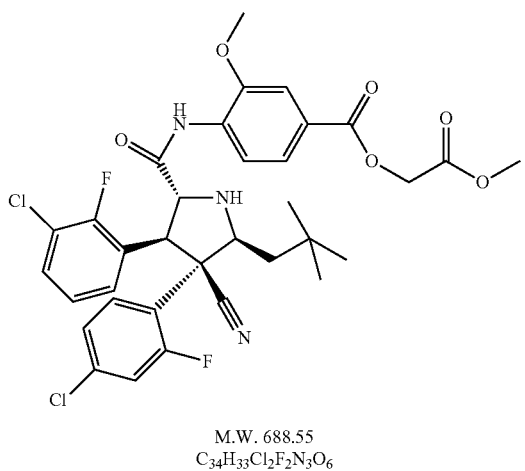 [SMILES: COC(=O)COC(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]

M.W. 688.55
$C_{34}H_{33}Cl_2F_2N_3O_6$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with methyl 2-hydroxyacetate to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid methoxycarbonylmethyl ester. MS (ES$^+$) m/z calcd. for $C_{34}H_{34}Cl_2F_2N_3O_6$: [(M+H)$^+$]: 688. found: 688.

Example 36

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 3-carboxy-propyl ester

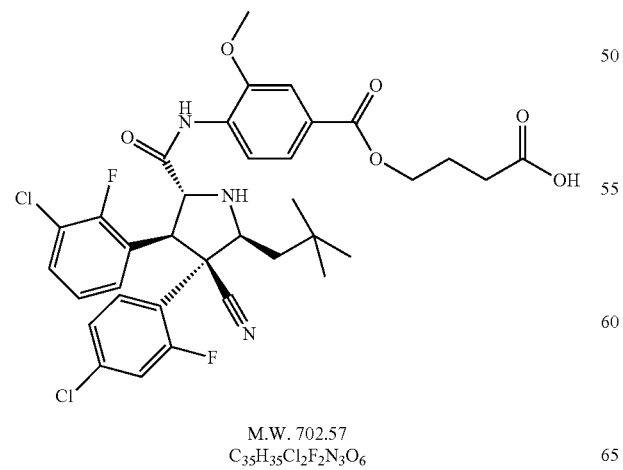

M.W. 702.57
$C_{35}H_{35}Cl_2F_2N_3O_6$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with tert-butyl 4-hydroxybutanoate to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 3-carboxy-propyl ester after removal of the Boc protection group by trifluoroacetic acid. MS (ES$^+$) m/z calcd. for $C_{35}H_{36}Cl_2F_2N_3O_6$: [(M+H)$^+$]: 702. found: 702.

Example 37

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-tert-butoxycarbonyl-ethyl ester

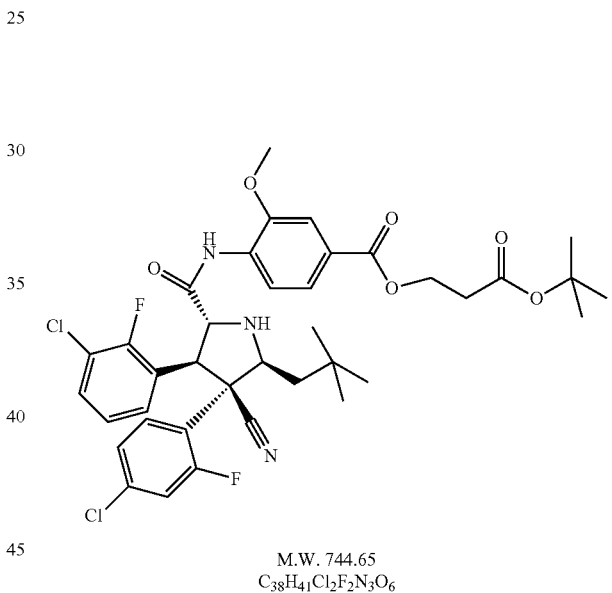

M.W. 744.65
$C_{38}H_{41}Cl_2F_2N_3O_6$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with tert-butyl 3-hydroxypropanoate to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-tert-butoxycarbonyl-ethyl ester. MS (ES$^+$) m/z calcd. for $C_{38}H_{42}Cl_2F_2N_3O_6$: [(M+H)$^+$]: 744. found: 744.

Example 38

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-carboxy-ethyl ester

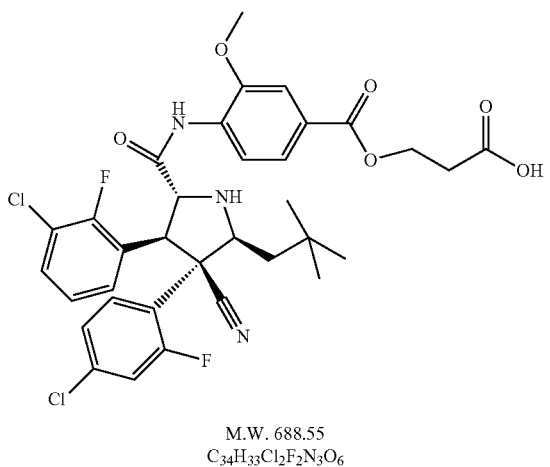 [SMILES: COc1cc(C(=O)OCCC(=O)O)ccc1NC(=O)[C@@H]1N[C@@H](CC(C)(C)C)[C@](C#N)(c2ccc(Cl)cc2F)[C@H]1c1cccc(Cl)c1F]

M.W. 688.55
$C_{34}H_{33}Cl_2F_2N_3O_6$

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-tert-butoxycarbonyl-ethyl ester was treated with trifluoro-acetic acid to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-carboxy-ethyl ester. MS (ES$^+$) m/z calcd. for $C_{34}H_{34}Cl_2F_2N_3O_6$: [(M+H)$^+$]: 688. found: 688.

Example 39

(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-hydrazinocarbonyl-2-methoxy-phenyl)-amide

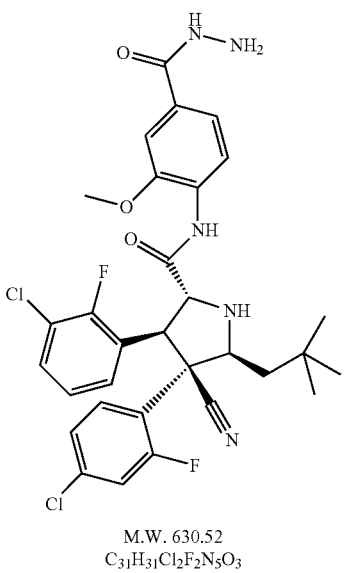 [SMILES: COc1cc(C(=O)NN)ccc1NC(=O)[C@@H]1N[C@@H](CC(C)(C)C)[C@](C#N)(c2ccc(Cl)cc2F)[C@H]1c1cccc(Cl)c1F]

M.W. 630.52
$C_{31}H_{31}Cl_2F_2N_5O_3$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with hydrazine to give (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-hydrazinocarbonyl-2-methoxy-phenyl)-amide. MS (ES$^+$) m/z calcd. for $C_{31}H_{32}Cl_2F_2N_5O_3$: [(M+H)$^+$]: 630. found: 630.

Example 40

(2S,3S,4S,5R,6S)-6-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-3,4,5-trihydroxy-tetrahydro-pyran-2-carboxylic acid; compound with trifluoro-acetic acid

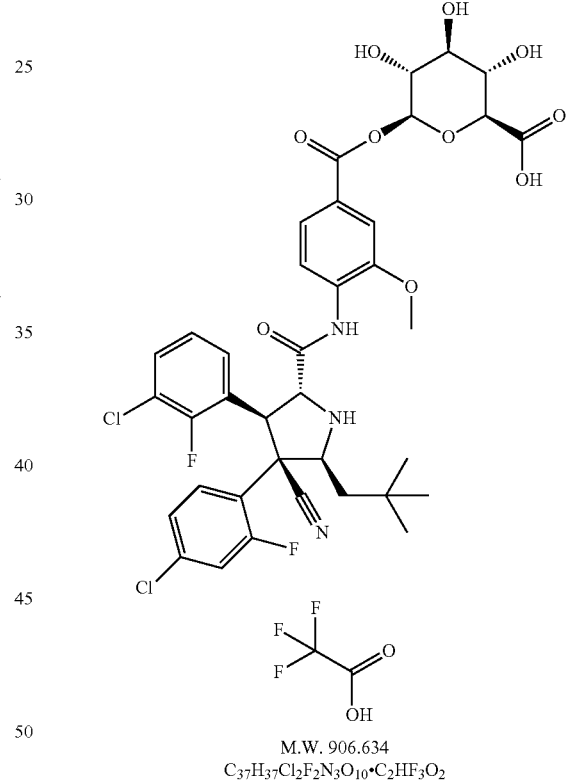

M.W. 906.634
$C_{37}H_{37}Cl_2F_2N_3O_{10}\cdot C_2HF_3O_2$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with (2S,3S,4S,5R)-benzyl 3,4,5,6-tetrahydroxytetrahydro-2H-pyran-2-carboxylate (prepared according to the procedure reported in Bowkett et al. *Tetrahedron* 2007, 63, 7596-7605) to give (2S,3S,4S,5R,6S)-benzyl 6-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)-3,4,5-trihydroxytetrahydro-2H-pyran-2-carboxylate.

(2S,3S,4S,5R,6S)-Benzyl 6-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxy-benzoyloxy)-3,4,5-trihydroxytetrahydro-2H-pyran-2-carboxylate (40 mg, 43.3 μmol) was dissolved in isopropanol (aided by sonication, 10 mL) then the 10% palladium on carbon (20 mg) was added. The flask was evacuated then refilled with hydrogen gas (2×, using a balloon). The reaction was stirred under hydrogen for 2 h. The reaction mixture was filtered, and the solids were washed with methanol. The filtrate was concentrated, and the crude residue was purified by high-performance liquid chromatography (C18, eluting with 50-95% acetonitrile-water) to give (2S,3S,4S,5R,6S)-6-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-3,4,5-trihydroxy-tetrahydro-pyran-2-carboxylic acid, trifluoroacetate salt, as white solids (32 mg, 77%). MS (ES$^+$) m/z calcd. for $C_{37}H_{38}Cl_2F_2N_3O_{10}$: [(M+H)$^+$]: 792. found: 792.

Example 41

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (2R,3S,4S,5R,6R)-3,4,5,6-tetrahydroxy-tetrahydro-pyran-2-ylmethyl ester; compound with trifluoro-acetic acid

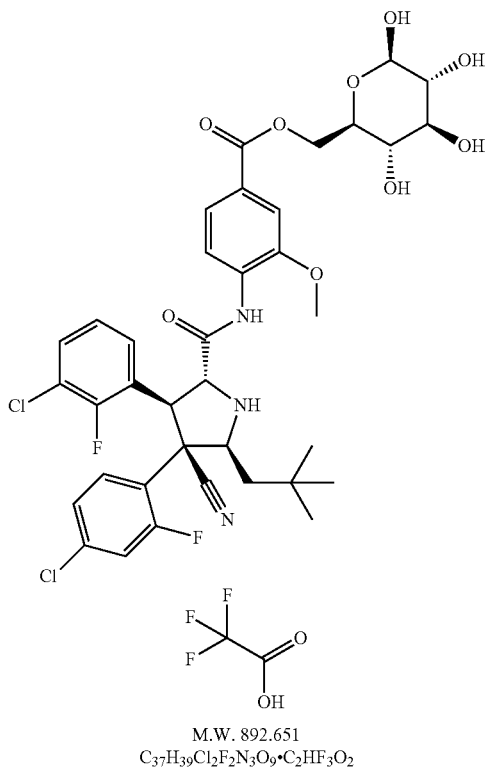

M.W. 892.651
$C_{37}H_{39}Cl_2F_2N_3O_9 \cdot C_2HF_3O_2$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with (2R,3R,4S,5S,6R)-6-(hydroxymethyl)tetrahydro-2H-pyran-2,3,4,5-tetraol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (2R,3S,4S,5R,6R)-3,4,5,6-tetrahydroxy-tetrahydro-pyran-2-ylmethyl ester; compound with trifluoro-acetic acid. MS (ES$^+$) m/z calcd. for $C_{37}H_{38}Cl_2F_2N_3O_9$: [(M+H)$^+$]: 780. found: 780.

Example 42

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, 2-(2-{2-[2-(2-{2-[2-(2-hydroxy-ethoxy)-ethoxy]-ethoxy}-ethoxy)-ethoxy]-ethoxy}-ethoxy)-ethyl ester, trifluoroacetate salt

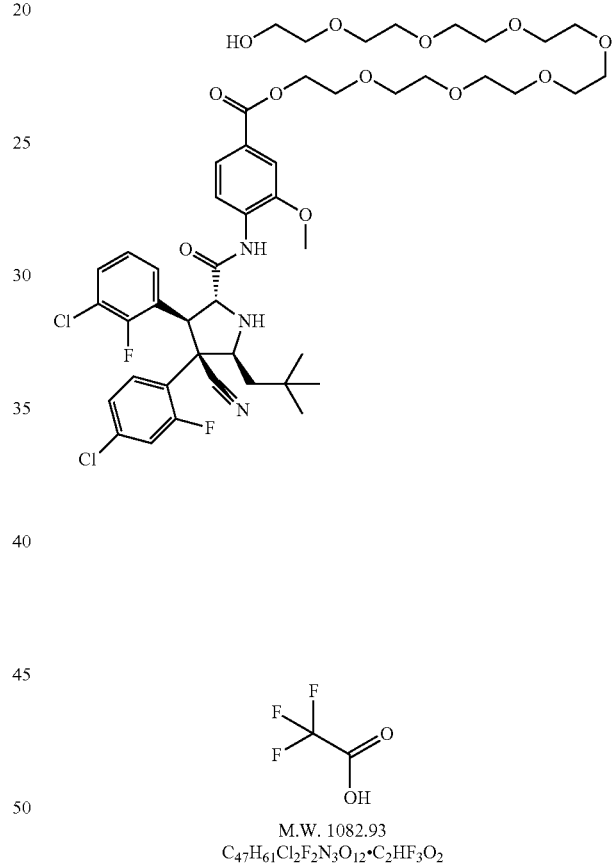

M.W. 1082.93
$C_{47}H_{61}Cl_2F_2N_3O_{12} \cdot C_2HF_3O_2$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 3,6,9,12,15,18,21-heptaoxatricosane-1,23-diol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, 2-(2-{2-[2-(2-{2-[2-(2-hydroxy-ethoxy)-ethoxy]-ethoxy}-ethoxy)-ethoxy]-ethoxy}-ethoxy)-ethyl ester, trifluoroacetate salt. MS (ES$^+$) m/z calcd. for $C_{47}H_{62}Cl_2F_2N_3O_{12}$: [(M+H)$^+$]970. found: 970.

Example 43

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, dodecaethylene glycol ester

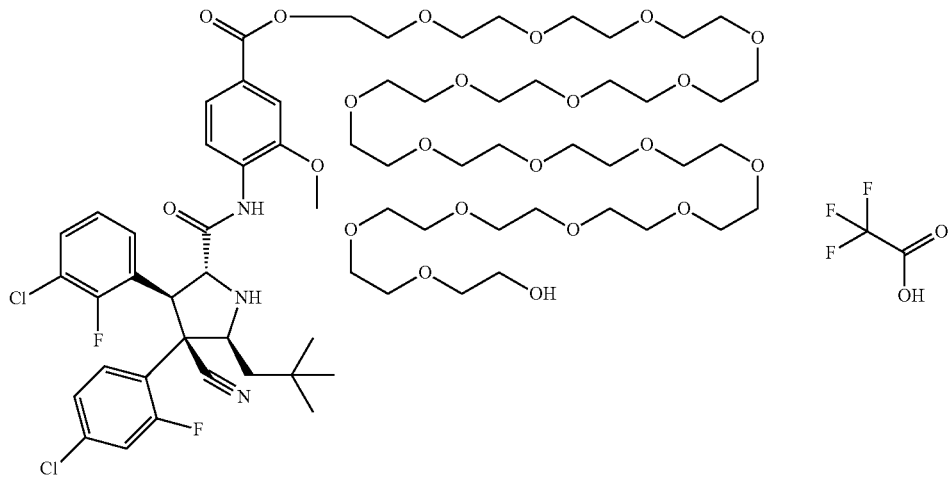

M.W. 1523.46
$C_{67}H_{101}Cl_2F_2N_3O_{22} \cdot C_2HF_3O_2$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with dodecaethylene glycol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, dodecaethylene glycol ester.

Example 44

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, polyethylene glycol-600 ester, trifluoroacetate salt

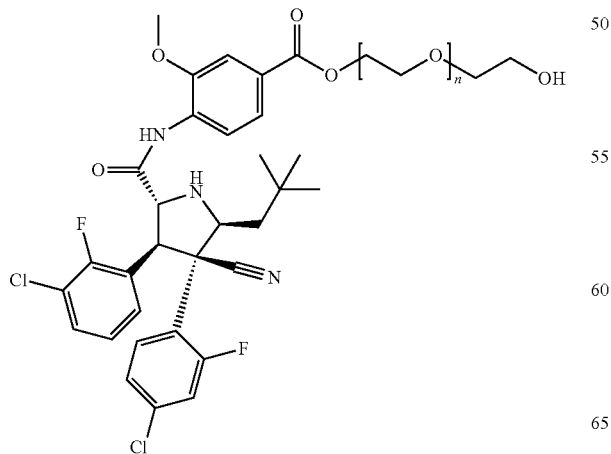

-continued

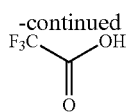

M.W. ~1198

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with polyethylene glycol-600 to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, polyethylene glycol-600 ester, trifluoroacetate salt.

Example 45

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, polyethylene glycol-200 ester, trifluoroacetate salt

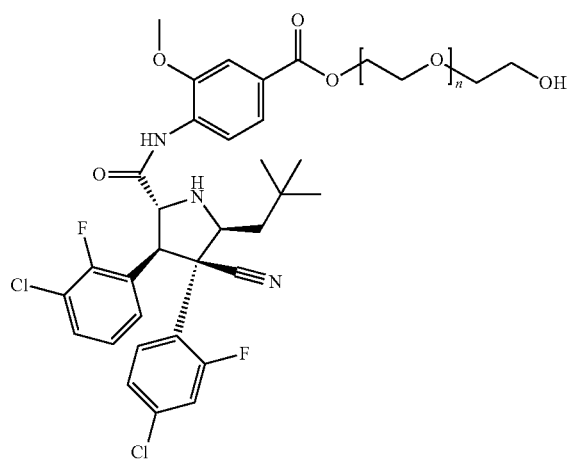

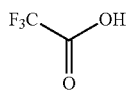

M.W. ~798

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with polyethylene glycol-200 to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, polyethylene glycol-200 ester, trifluoroacetate salt.

Example 46

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-dimethylamino-ethoxy)-ethyl ester, hydrochloride

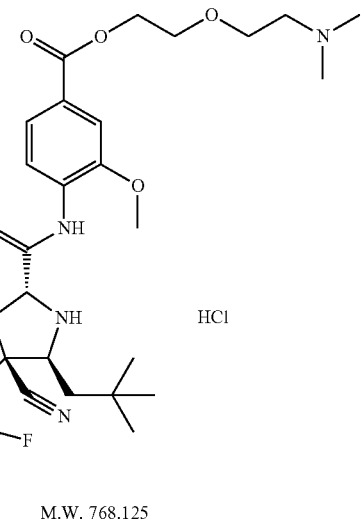

M.W. 768.125
$C_{37}H_{42}Cl_2F_2N_4O_5 \cdot HCl$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 2-(2-(dimethylamino)ethoxy)ethanol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-dimethylamino-ethoxy)-ethyl ester, hydrochloride. MS (ES$^+$) m/z calcd. for $C_{37}H_{42}Cl_2F_2N_4O_5$: (M$^+$): 731. found: 731.

Example 47

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(2-hydroxy-ethoxy)-ethoxy]-ethyl ester, hydrochloride

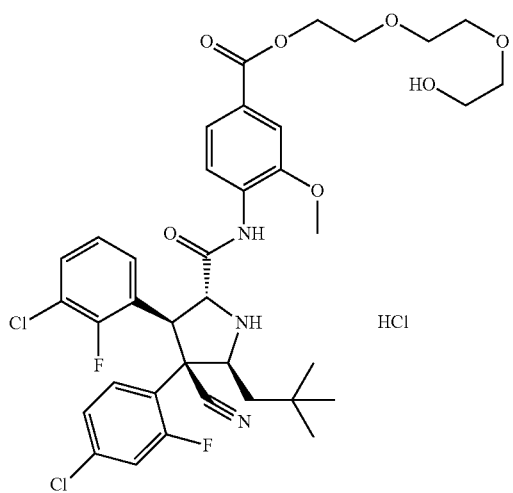

M.W. 785.108
$C_{37}H_{41}Cl_2F_2N_3O_7 \cdot HCl$

Example 48

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(2-methoxy-ethoxy)-ethoxy]-ethyl ester, hydrochloride

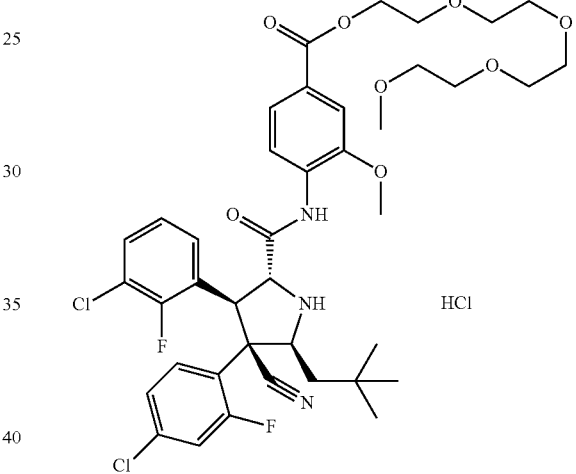

M.W. 799.135
$C_{38}H_{43}Cl_2F_2N_3O_7 \cdot HCl$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 2,2'-(ethane-1,2-diyl-bis(oxy))diethanol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(2-hydroxy-ethoxy)-ethoxy]-ethyl ester, hydrochloride. MS (ES$^+$) m/z calcd. for $C_{37}H_{41}Cl_2F_2N_3O_7$: [(M)$^+$]748. found: 748.

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 2-(2-(2-methoxy-ethoxy)ethoxy)ethanol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(2-methoxy-ethoxy)-ethoxy]-ethyl ester, hydrochloride. MS (ES$^+$) m/z calcd. for $C_{38}H_{43}Cl_2F_2N_3O_7$: [(M)$^+$]762. found: 762.

Example 49

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-methoxy-ethoxy)-ethoxy]-ethoxy}-ethyl ester, hydrochloride

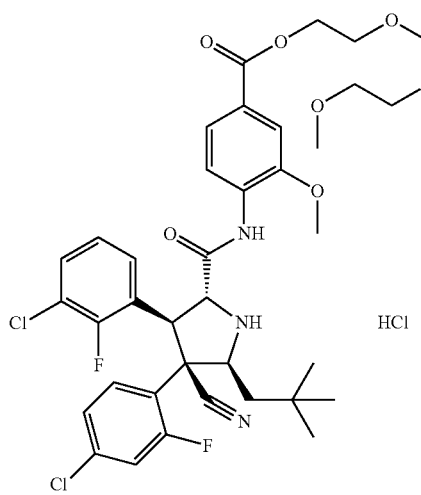

M.W. 843.187
$C_{40}H_{47}Cl_2F_2N_3O_8$•HCl

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 2,5,8,11-tetraoxamidecan-13-ol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-methoxy-ethoxy)-ethoxy]-ethoxy}-ethyl ester, hydrochloride. MS (ES$^+$) m/z calcd. for $C_{40}H_{47}Cl_2F_2N_3O_8$: [(M)$^+$]806. found: 806.

Example 50

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-{2-[2-(2-hydroxy-ethoxy)-ethoxy]-ethoxy}-ethoxy)-ethyl ester, hydrochloride

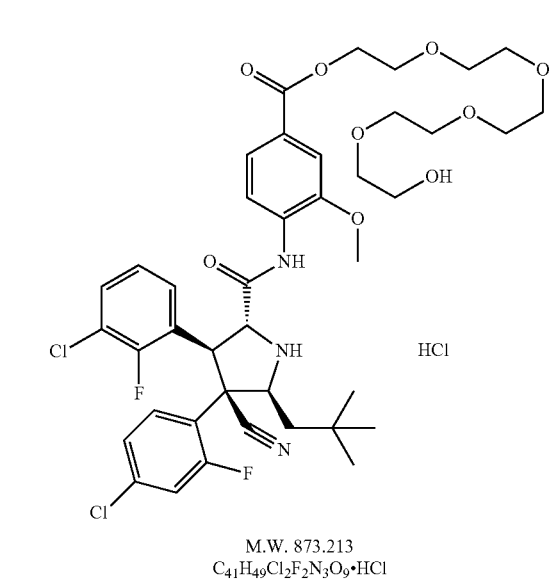 [SMILES: COc1cc(C(=O)OCCOCCOCCOCCOCCO)ccc1NC(=O)[C@@H]1N[C@@H](CC(C)(C)C)[C@](C#N)(c2ccc(Cl)cc2F)[C@H]1c1cccc(Cl)c1F ; Cl]

M.W. 873.213
$C_{41}H_{49}Cl_2F_2N_3O_9$•HCl

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 3,6,9,12-tetraoxatetradecane-1,14-diol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-{2-[2-(2-hydroxy-ethoxy)-ethoxy]-ethoxy}-ethoxy)-ethyl ester, hydrochloride. MS (ES$^+$) m/z calcd. for $C_{41}H_{50}Cl_2F_2N_3O_9$: [(M+H)$^+$]836. found: 836.

Example 51

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-{2-[2-(2-methoxy-ethoxy)-ethoxy]-ethoxy}-ethoxy)-ethyl ester, hydrochloride

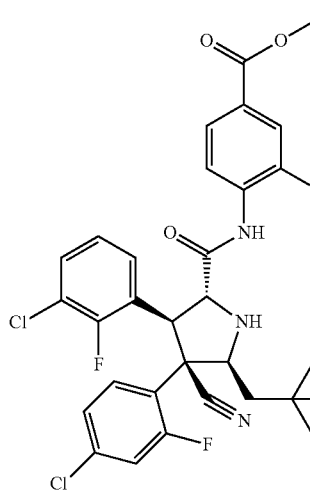

M.W. 887.24
$C_{42}H_{51}Cl_2F_2N_3O_9 \cdot HCl$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 2,5,8,11,14-pentaoxa-hexadecan-16-ol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(2-{2-[2-(2-methoxy-ethoxy)-ethoxy]-ethoxy}-ethoxy)-ethyl ester, hydrochloride. MS (ES$^+$) m/z calcd. for $C_{42}H_{52}Cl_2F_2N_3O_9$: [(M+H)$^+$]851. found: 851.

Example 52

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(2-{2-[2-(2-hydroxy-ethoxy)-ethoxy]-ethoxy}-ethoxy)-ethoxy]-ethyl ester, hydrochloride

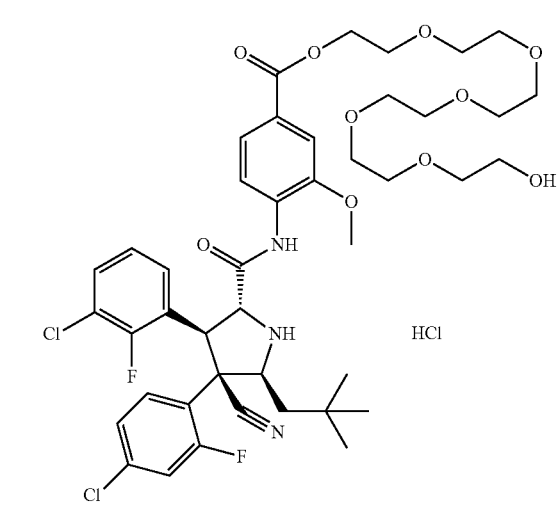

M.W. 917.266
$C_{43}H_{53}Cl_2F_2N_3O_{10} \cdot HCl$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 3,6,9,12,15-pentaoxa-heptadecane-1,17-diol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(2-{2-[2-(2-hydroxy-ethoxy)-ethoxy]-ethoxy}-ethoxy)-ethoxy]-ethyl ester, hydrochloride. MS (ES$^+$) m/z calcd. for $C_{43}H_{54}Cl_2F_2N_3O_{10}$: [(M+H)$^+$]880. found: 880.

Example 53

(R)-2-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoylamino)-pentanedioic acid dimethyl ester, hydrochloride

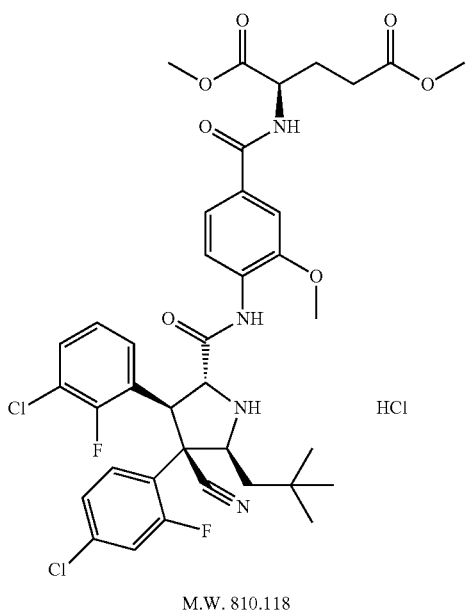

M.W. 810.118
$C_{38}H_{40}Cl_2F_2N_4O_7 \cdot HCl$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with (R)-dimethyl 2-aminopentanedioate to give (R)-2-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoylamino)-pentanedioic acid dimethyl ester, hydrochloride. MS (ES+) m/z calcd. for $C_{38}H_{41}Cl_2F_2N_4O_7$: [(M+H)+]773. found: 773.

Example 54

(R)-2-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoylamino)-pentanedioic acid, hydrochloride

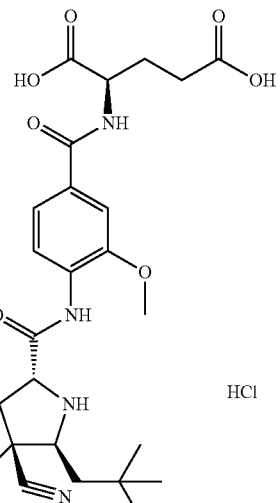

M.W. 782.064 $C_{36}H_{36}Cl_2F_2N_4O_7 \cdot HCl$ (R)-2-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoylamino)-pentanedioic acid dimethyl ester, hydrochloride (200 mg, 259 µmol) was suspended in 5 mL of tetrahydrofuran/water (4/1 ratio) then lithium hydroxide (100 mg) was added. After stirring at room temperature for 4 h, the reaction mixture was filtered, and the crude residue was purified by high-performance liquid chromatography (C18, eluting with 40-95% acetonitrile-water) to give (R)-2-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoylamino)-pentanedioic acid, hydrochloride after lyophilization with acetonitrile and 1N solution of hydrochloric acid. MS (ES⁺) m/z calcd. for $C_{36}H_{37}Cl_2F_2N_4O_7$: [(M+H)⁺]745. found: 745.

Example 55

(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid {2-methoxy-4-[methyl-((2S,3R,4R,5R)-2,3,4,5,6-pentahydroxy-hexyl)-carbamoyl]-phenyl}-amide, hydrochloride

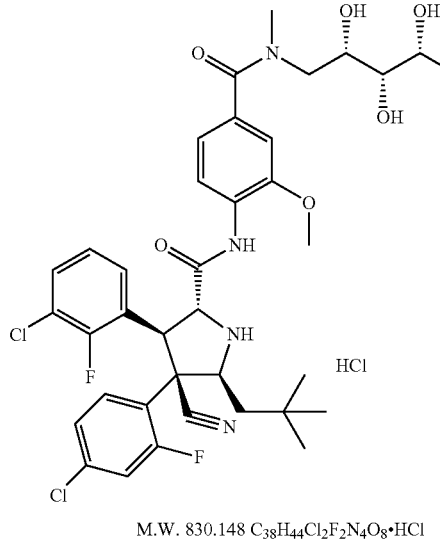

M.W. 830.148 $C_{38}H_{44}Cl_2F_2N_4O_8 \cdot HCl$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with (2R,3R,4R,5S)-6-(methylamino)-hexane-1,2,3,4,5-pentaol to give (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid {2-methoxy-4-[methyl-((2S,3R,4R,5R)-2,3,4,5,6-pentahydroxy-hexyl)-carbamoyl]-phenyl}-amide, hydrochloride. MS (ES⁺) m/z calcd. for $C_{38}H_{45}Cl_2F_2N_4O_8$: [(M+H)⁺]793. found: 793.

Example 56

(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [2-methoxy-4-((2S,3R,4R,5S,6R)-2,4,5-trihydroxy-6-hydroxymethyl-tetrahydro-pyran-3-ylcarbamoyl)-phenyl]-amide, hydrochloride

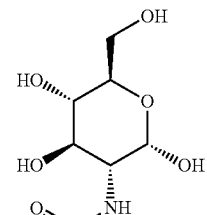
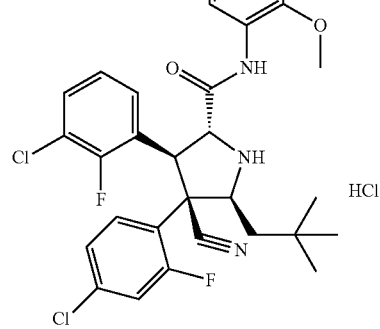

M.W. 814.106 $C_{37}H_{40}Cl_2F_2N_4O_8 \cdot HCl$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with (2S,3R,4R,5S,6R)-3-amino-6-(hydroxymethyl)tetrahydro-2H-pyran-2,4,5-triol hydrochloride to give (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid [2-methoxy-4-((2S,3R,4R,5S,6R)-2,4,5-trihydroxy-6-hydroxymethyltetrahydro-pyran-3-ylcarbamoyl)-phenyl]-amide, hydrochloride. MS (ES+) m/z calcd. for $C_{37}H_{41}Cl_2F_2N_4O_8$: [(M+H)+]777. found: 777.

Example 57

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-hydroxy-ethoxy)-ethoxy]-ethoxy}-ethyl ester, hydrochloride

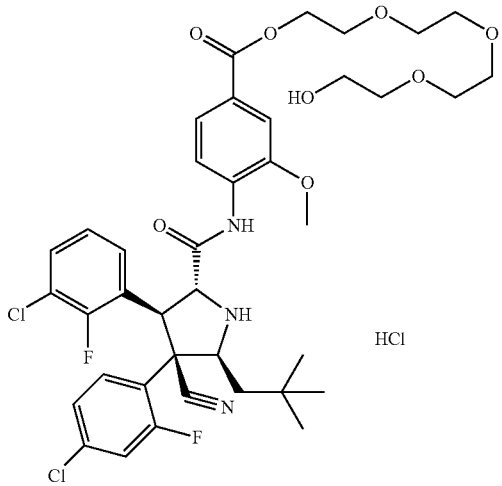

M.W. 829.16 $C_{39}H_{45}Cl_2F_2N_3O_8$·HCl amide, hydrochloride. MS (ES+) m/z calcd. for $C_{39}H_{46}Cl_2F_2N_3O_8$: [(M+H)+]792. found: 792.

Example 58

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-350 ester, trifluoroacetate salt

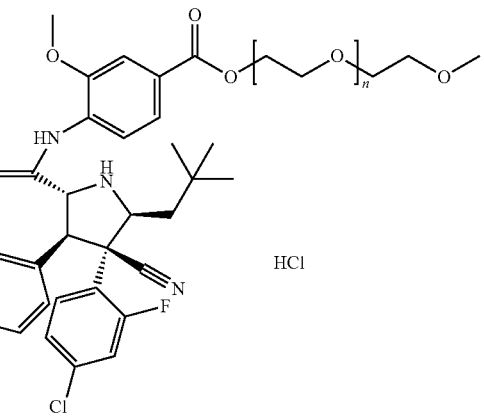

M.W. ~948

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 2,2'-(2,2'-oxybis (ethane-2,1-diyl)bis(oxy))diethanol to give (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid [2-methoxy-4-((2S,3R,4R,5S,6R)-2,4,5-trihydroxy-6-hydroxymethyl-tetrahydro-pyran-3-ylcarbamoyl)-phenyl]-

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with polyethylene glycol-350 mono methyl ether (mPEG-350) to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-350 ester, hydrochloride.

Example 59

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-550 ester, hydrochloride

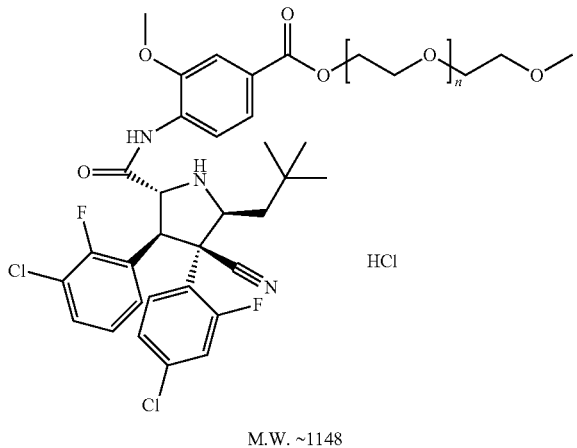

M.W. ~1148

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with polyethylene glycol-550 mono methyl ether (mPEG-550) to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-550 ester, hydrochloride.

Example 60

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, 2-[4-(2-hydroxy-ethyl)-piperazin-1-yl]-ethyl ester, dimer

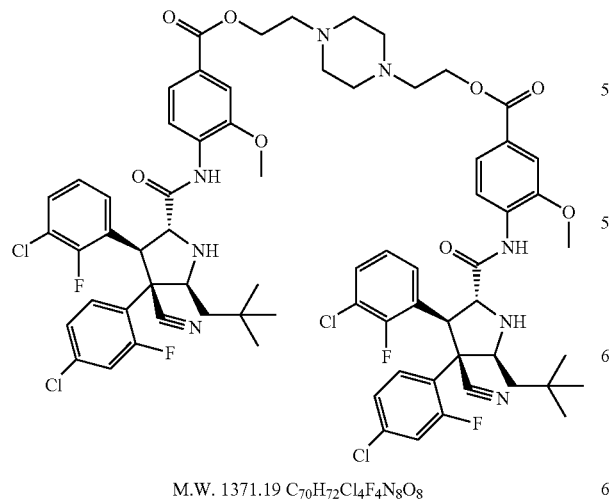

M.W. 1371.19 $C_{70}H_{72}Cl_4F_4N_8O_8$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 2,2'-(piperazine-1,4-diyl)diethanol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[4-(2-hydroxy-ethyl)-piperazin-1-yl]-ethyl ester, dimer. MS (ES$^+$) m/z calcd. for $C_{70}H_{73}Cl_4F_4N_8O_8$: [(M+H)$^+$]1369. found: 1369.

Example 61

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[4-(2-hydroxy-ethyl)-piperazin-1-yl]-ethyl ester

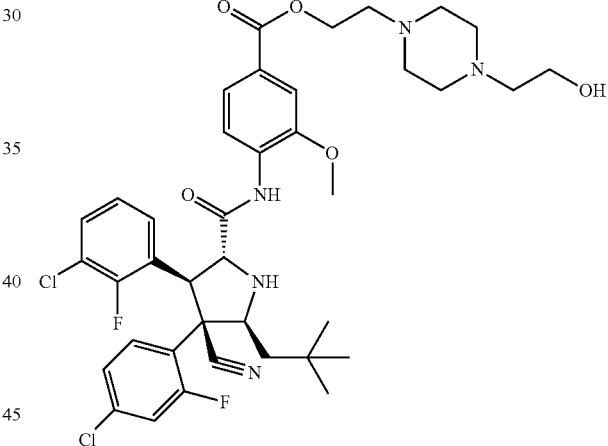

M.W. 772.716 $C_{39}H_{45}Cl_2F_2N_5O_5$

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with 2,2'-(piperazine-1,4-diyl)diethanol to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[4-(2-hydroxy-ethyl)-piperazin-1-yl]-ethyl ester. MS (ES$^+$) m/z calcd. for $C_{39}H_{46}Cl_2F_2N_5O_5$: [(M+H)$^+$]772. found: 772.

Example 62

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[4-(2-hydroxy-ethyl)-piperazin-1-yl]-ethyl ester, PEG-400 ester, hydrochloride salt

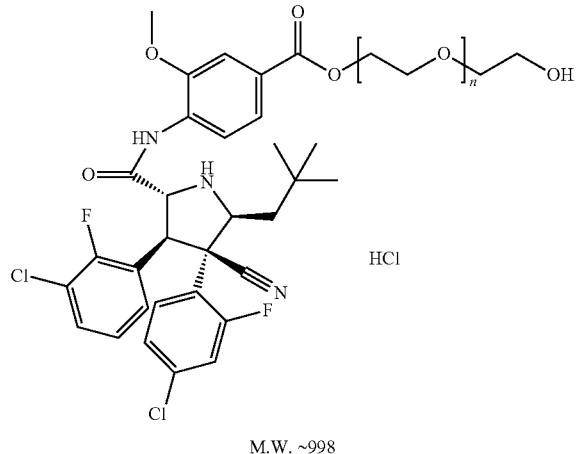

M.W. ~998

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with polyethylene glycol-400 (PEG-400) to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, PEG-400 ester, hydrochloride.

Example 63

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[4-(2-hydroxy-ethyl)-piperazin-1-yl]-ethyl ester, mPEG-750 ester, hydrochloride salt

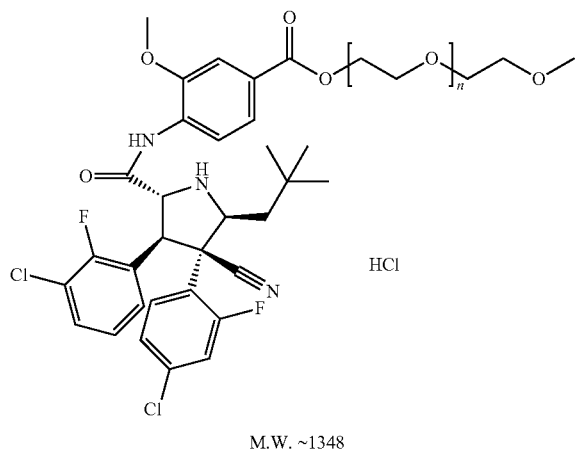

M.W. ~1348

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with polyethylene glycol-750 mono methyl ether (mPEG-750) to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-750 ester, hydrochloride.

Example 64

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(4-methyl-piperazin-1-yl)-2-oxo-ethyl ester, hydrochloride

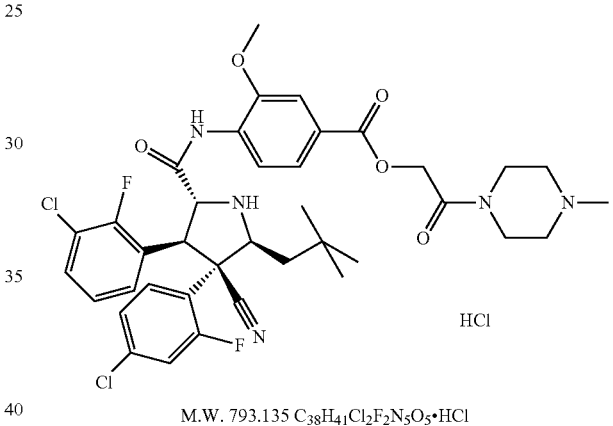

M.W. 793.135 $C_{38}H_{41}Cl_2F_2N_5O_5 \cdot HCl$

In a 15 mL pressure tube, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1, 100 mg, 162 µmol), 2-chloro-1-(4-methylpiperazin-1-yl)ethanone, hydrochloride (34.6 mg, 162 µmol) and cesium carbonate (111 mg, 341 µmol) were combined with dry dimethyl formamide (2 mL) to give a white suspension. The tube was capped and heated at 50° C. with stirring. After 1.5 h, the reaction mixture was cooled down to room temperature. It was poured into water and extracted with methylene chloride (2×). The methylene chloride layers were combined, dried over anhydrous sodium sulfate, filtered and concentrated. The residue was purified by flash chromatography (24 g pre-packed silica gel column, eluted with methanol in methylene chloride) to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-(4-methyl-piperazin-1-yl)-2-oxo-ethyl ester, hydrochloride as an off-white solid (99 mg, 81% yield). The product was mixed with acetonitrile (2 mL) to form a suspension. A few drops of 1N aqueous hydrochloric acid were added to the mixture. The suspension became clear solution. It was frozen and lyophilized to give an off-white solid as hydrochloride salt. LCMS (ES+) m/z calcd. for $C_{38}H_{42}Cl_2F_2N_5O_5$ [(M+H)+]: 756. found: 756.

Example 65

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid carbamoylmethyl ester

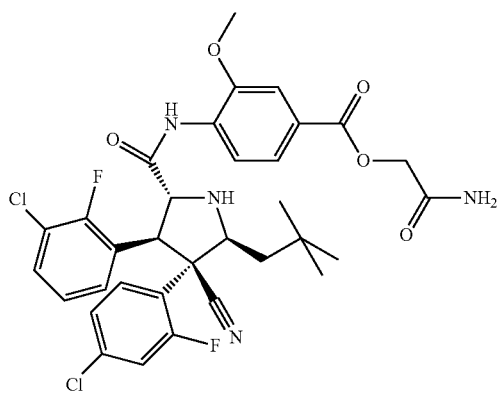

M.W. 673.53 $C_{33}H_{32}Cl_2F_2N_4O_5$

In a 15 mL pressure tube, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1, 100 mg, 162 μmol) and cesium carbonate (63.4 mg, 195 μmol) were combined with dimethyl formamide (2 mL). 2-Chloroacetamide (15.2 mg, 162 μmol) was added to the mixture with stirring to give a white suspension. The tube was capped and heated at 50° C. overnight. The reaction mixture was cooled down to room temperature. It was poured into water and extracted with ethyl acetate (2×). The ethyl acetate layers were combined, dried over anhydrous sodium sulfate, filtered and concentrated. The residue was purified with flash chromatography (24 g pre-packed silica gel column, eluted with ethyl acetate in hexanes) to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid carbamoylmethyl ester as an off-white solid (62 mg, 58% yield). LCMS (ES+) m/z calcd. for $C_{33}H_{33}Cl_2F_2N_4O_5$ [(M+H)+]: 673. found: 673.

Example 66

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-morpholin-4-yl-2-oxo-ethyl ester

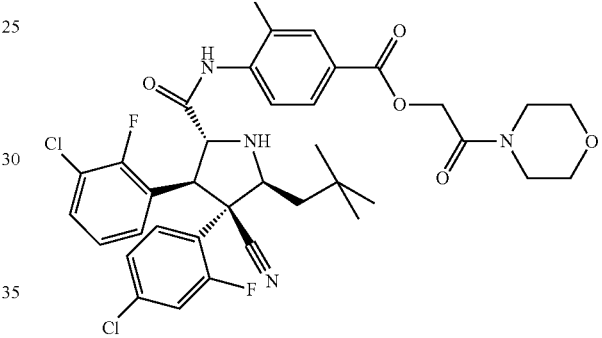

M.W. 743.62 $C_{37}H_{38}Cl_2F_2N_4O_6$

In a 15 mL pressure tube, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1, 100 mg, 162 μmol) and cesium carbonate (63.4 mg, 195 μmol) were combined with dry dimethyl formamide (5 mL). 2-Chloro-1-morpholinoethanone (26.5 mg, 21.1 μL, 162 μmol) was added to the mixture with stirring. The tube was capped and heated at 50° C. After 1.5 h, the reaction mixture was cooled down to room temperature. It was poured into water and extracted with ethyl acetate (2×). The ethyl acetate layers were combined, dried over anhydrous sodium sulfate, filtered and concentrated. The residue was purified with flash chromatography (24 g pre-packed silica gel column, eluted with ethyl acetate in hexanes) to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-morpholin-4-yl-2-oxoethyl ester as an off-white solid (104 mg, 86% yield) as product. LCMS (ES+) m/z calcd. for $C_{37}H_{39}Cl_2F_2N_4O_6$ [(M+H)+]: 743. found: 743.

Example 67

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid [(2,2-dimethyl-[1,3]dioxolan-4-ylmethyl)-carbamoyl]-methyl ester

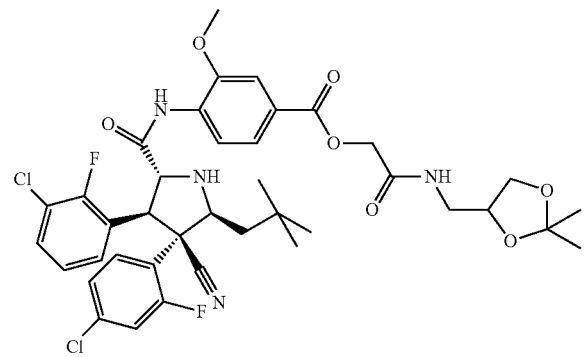

M.W. 787.68 $C_{39}H_{43}Cl_2F_2N_4O_7$

In a 15 mL pressure tube, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1, 300 mg, 487 μmol) and 2-chloro-N-((2,2-dimethyl-1,3-dioxolan-4-yl)methyl)acetamide (101 mg, 487 μmol) were combined with dry dimethyl formamide (5 mL) to give a white suspension. The tube was capped and heated at 50° C. overnight. The reaction mixture was cooled down to room temperature. It was poured into water and extracted with ethyl acetate (2×). The ethyl acetate layers were combined, dried over anhydrous sodium sulfate, filtered and concentrated. The residue was purified with flash chromatography (24 g pre-packed silica gel column, eluted with methanol in ethyl acetate) to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid [(2,2-dimethyl-[1,3]dioxolan-4-ylmethyl)-carbamoyl]-methyl ester as an off-white solid (92 mg, 24% yield). LCMS (ES+) m/z calcd. for $C_{39}H_{42}Cl_2F_2N_4O_7$ [(M+H)+]: 787. found: 787.

Example 68

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (2,3-dihydroxy-propylcarbamoyl)-methyl ester

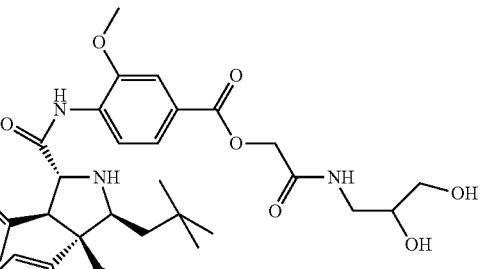

M.W. 747.61 $C_{36}H_{38}Cl_2F_2N_4O_7$

In a 4 dram vial, 2-((2,2-dimethyl-1,3-dioxolan-4-yl)methylamino)-2-oxoethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (Example 67, 67 mg, 85.1 μmol) was combined with methanol (1 mL), methylene chloride (0.5 mL) and water (2 drops) to give a colorless solution. Trifluoroacetic acid (19.4 mg, 13.1 μL, 170 μmol) was added. The reaction mixture was stirred at room temperature for 5 h then concentrated. The residue was reconstituted with methylene chloride (100 mL). It was washed with saturated aqueous sodium carbonate solution, then brine. The organic layer was dried over anhydrous sodium sulfate, filtered and concentrated. The crude residuw was purified by flash chromatography (23 g SUPELCO spherical silica gel column, eluted with methanol in ethyl acetate) to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (2,3-dihydroxy-propylcarbamoyl)-methyl ester (23 mg, 36% yield). LCMS (ES$^+$) m/z calcd. for C$_{36}$H$_{39}$Cl$_2$F$_2$N$_4$O$_7$ [(M+H)$^+$]: 747. found: 747.

Example 69

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid carboxymethyl ester

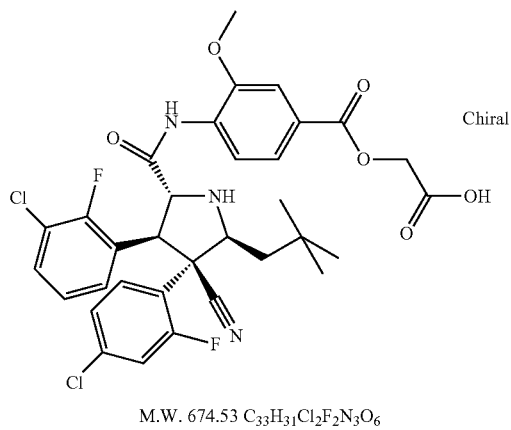 [SMILES: COc1cc(C(=O)OCC(=O)O)ccc1NC(=O)[C@@H]1N[C@@H](CC(C)(C)C)[C@](C#N)(c2ccc(Cl)cc2F)[C@H]1c1cccc(Cl)c1F]

M.W. 674.53  C$_{33}$H$_{31}$Cl$_2$F$_2$N$_3$O$_6$

In a 50 mL pressure tube, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1, 1 g, 1.62 mmol), tert-butyl 2-bromoacetate (316 mg, 240 µL, 1.62 mmol) and cesium carbonate (634 mg, 1.95 mmol) were combined with dry dimethyl formamide (10 mL) to give a white suspension. The tube was capped and heated at 50° C. After 10 min, the reaction mixture was cooled down to room temperature, poured into water and extracted with ethyl acetate (2×). The combined ethyl acetate layers were washed with brine solution, dried over anhydrous sodium sulfate, filtered and concentrated to give 2-tert-butoxy-2-oxoethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as light yellow solid (1280 mg), which was used without further purification.

In a 25 mL round-bottomed flask, 45% hydrogen bromide in acetic acid (10 mL, 794 µmol) was added. It was cooled down to 0° C., then 2-tert-butoxy-2-oxoethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (580 mg, 794 µmol) was added as solid. After 30 min, the reaction mixture was concentrated, and water (50 mL) was added to the residue. It was extracted with methylene chloride (2×300 mL). The methylene chloride layers were combined, dried over anhydrous sodium sulfate, filtered and concentrated to give a crude product, which was purified by filtering through a short plug of silica gel to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid carboxymethyl ester as an off white solid (530 mg, 99% yield). LCMS (ES$^+$) m/z calcd. for C$_{33}$H$_{32}$Cl$_2$F$_2$N$_3$O$_6$ [(M+H)$^+$]: 674. found: 674.

Example 70

(S)-2-[2-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-acetylamino]-pentanedioic acid dibenzyl ester

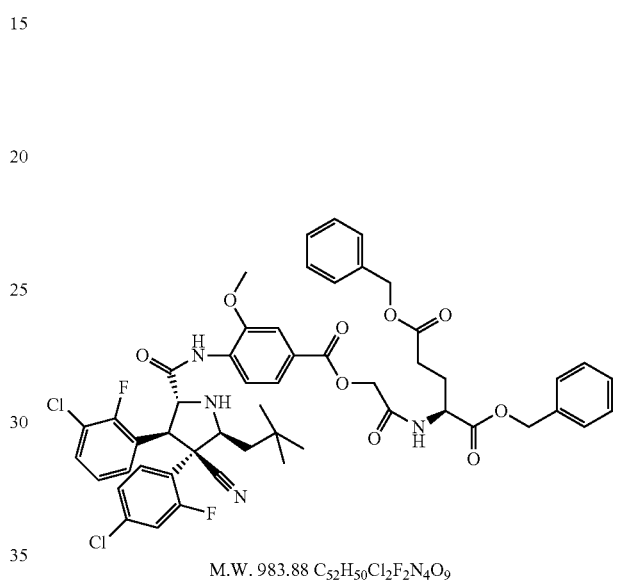

M.W. 983.88  C$_{52}$H$_{50}$Cl$_2$F$_2$N$_4$O$_9$

In a 20 mL round-bottomed flask, 2-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxy-benzoyloxy)-acetic acid (Example 69, 133 mg, 197 µmol), HATU (75.0 mg, 197 µmol) and Hunig's base (51.0 mg, 68.9 µL, 394 µmol) were combined with dry tetrahydrofuran (1 mL) to give an off-white suspension at room temperature. The mixture was stirred for 30 min and a solution of (S)-dibenzyl 2-aminopentanedioate hydrochloride (108 mg, 296 µmol) and Hunig's base (2 eq.) in dry tetrahydrofuran (1 mL) was added. After 1 h, the reaction mix was directly purified with reverse phase high-performance liquid chromatography to isolate the desired fraction, which was neutralized with saturated aqueous sodium carbonate solution, extracted with methylene chloride. The methylene chloride layer was washed with water and brine, dried over anhydrous sodium sulfate, filtered and concentrated to give (S)-2-[2-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-acetylamino]-pentanedioic acid dibenzyl ester (63 mg, 33% yield). LCMS (ES$^+$) m/z calcd. for C$_{52}$H$_{51}$Cl$_2$F$_2$N$_4$O$_9$ [(M+H)$^+$]: 983. found: 983.

Example 71

(S)-2-[2-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-acetylamino]-pentanedioic acid

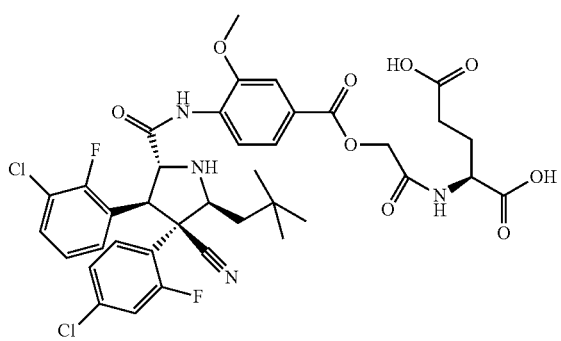

M.W. 803.63 C₃₈H₃₈Cl₂F₂N₄O₉

In a 25 mL three-necked flask, (S)-dibenzyl 2-(2-(4-(((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)acetamido)pentanedioate (Example 70, 61 mg, 62.0 µmol) was combined with isopropanol (5 mL) at room temperature. Then palladium on carbon (33.0 mg, 31.0 µmol) was added. The flask was flushed with nitrogen, and then replaced with hydrogen. It was stirred at room temperature under hydrogen balloon. After 30 min, the reaction mix was filtered through a Celite cake to remove the catalyst. The Celite cake was washed thoroughly with isopropanol. The filtrate and washing solutions were combined and concentrated to give a crude product, which was purified with reverse phase high-performance liquid chromatography. The pure fractions were concentrated and lyophilized to give (S)-2-[2-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-acetylamino]-pentanedioic acid as a white product (20 mg, 33% yield). LCMS (ES⁺) m/z calcd. for $C_{38}H_{39}Cl_2F_2N_4O_9$ [(M+H)⁺]: 803. found: 803.

Example 72

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(2-methoxy-ethoxy)-ethoxy]-ethoxycarbonylmethyl ester

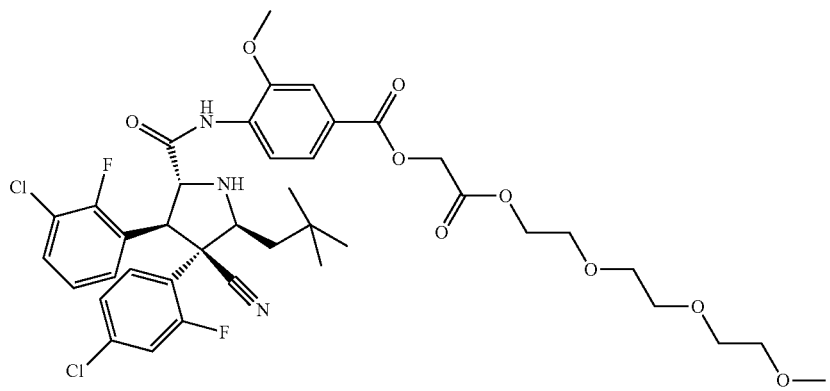

M.W. 820.7 C₄₀H₄₅Cl₂F₂N₃O₉

In a 20 mL round-bottomed flask, 2-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxy-benzoyloxy)acetic acid (Example 69, 150 mg, 222 µmol), HATU (84.6 mg, 222 µmol) and Hunig's base (86.2 mg, 117 µL, 667 µmol) were combined with dry tetrahydrofuran (1 mL) to give a light brown suspension at room temperature. It was stirred for 30 min and the solution became clear. Triethylene glycol monomethyl ether (76.9 mg, 73.4 µL, 445 µmol) was added drop wise to the mixture. After stirring at room temperature overnight, the reaction mixture was concentrated. The residue was reconstituted with ethyl acetate. It was washed with water and brine, dried over anhydrous sodium sulfate, filtered and concentrated. The residue was absorbed on small amount of silica gel and loaded on a 24 g pre-packed silica gel column. Eluting the column with ethyl acetate gave 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-[2-(2-methoxy-ethoxy)-ethoxy]-ethoxycarbonylmethyl ester as an off-white solid (65 mg, 35% yield). LCMS (ES⁺) m/z calcd. for $C_{40}H_{46}Cl_2F_2N_3O_9$ [(M+H)⁺]: 820. found: 820.

Example 73

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-methoxy-ethoxy)-ethoxy]-ethoxy}-ethoxycarbonylmethyl ester

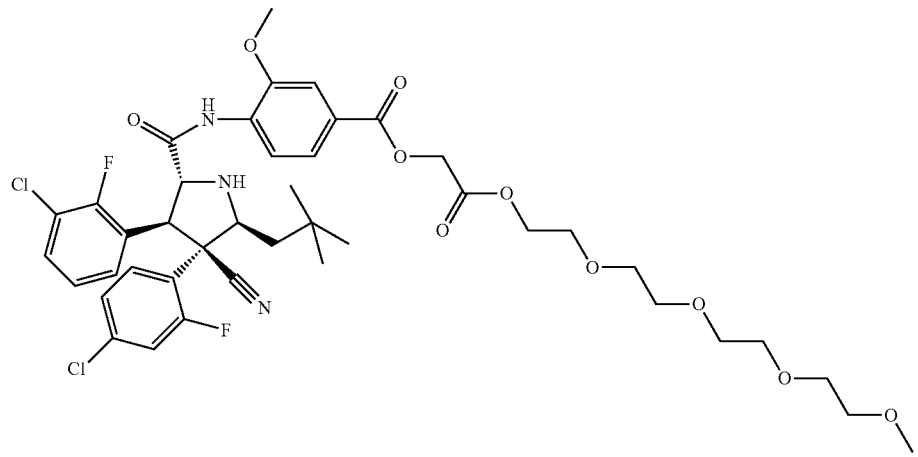

M.W. 864.76 C$_{42}$H$_{49}$Cl$_2$F$_2$N$_3$O$_{10}$

In a 20 mL round-bottomed flask, 2-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxy-benzoyloxy)-acetic acid (Example 69, 150 mg, 222 µmol), HATU (84.6 mg, 222 µmol) and Hunig's base (86.2 mg, 117 µL, 667 µmol) were combined with dry tetrahydrofuran (2 mL) to give an off-white suspension at room temperature. It was stirred at room temperature for 30 min, and the solution became clear. 2,5,8,11-Tetraoxamidecan-13-ol (94.5 mg, 90.4 µL, 445 µmol) was added. The mixture was stirred at room temperature overnight then concentrated. The residue was reconstituted with ethyl acetate. It was washed with water and brine, dried over anhydrous sodium sulfate, filtered and concentrated. The residue was absorbed on small amount of silica gel and loaded on a 24 g pre-packed silica gel column. Eluting the column with ethyl acetate gave 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-methoxy-ethoxy)-ethoxy]-ethoxy}-ethoxycarbonylmethyl ester as an off-white solid (19 mg, 10% yield). LCMS (ES⁺) m/z calcd. for C$_{42}$H$_{50}$Cl$_2$F$_2$N$_3$O$_{10}$ [(M+H)⁺]: 864. found: 864.

Example 74

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid [2-(2-hydroxy-ethoxy)-ethylcarbamoyl]-methyl ester

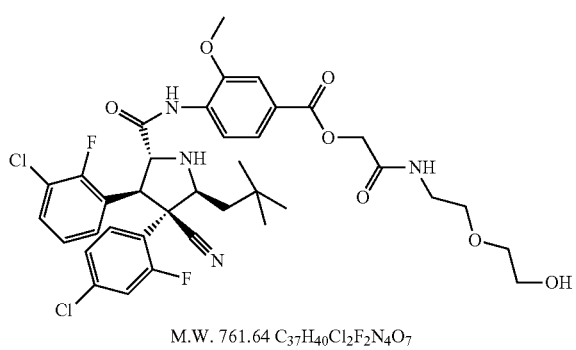 [SMILES: COc1cc(C(=O)OCC(=O)NCCOCCO)ccc1NC(=O)[C@@H]1N[C@@H](CC(C)(C)C)[C@](C#N)(c2ccc(Cl)cc2F)[C@H]1c1cccc(Cl)c1F]

M.W. 761.64 C$_{37}$H$_{40}$Cl$_2$F$_2$N$_4$O$_7$

In a 20 mL round-bottomed flask, 2-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)acetic acid (Example 69, 150 mg, 152 µL, 222 µmol), HATU (84.6 mg, 222 µmol) and Hunig's base (86.2 mg, 117 µL, 667 µmol) were combined with dry tetrahydrofuran (2 mL) to give an off-white suspension at room temperature. It was stirred for 30 min and the solution became clear. 2-(2-Aminoethoxy)ethanol (23.4 mg, 16.0 µL, 222 µmol) was added. After stirring at room temperature overnight, the reaction mixture was concentrated. The residue was reconstituted with ethyl acetate. It was washed with water and brine, dried over anhydrous sodium sulfate, filtered and concentrated. The residue was absorbed on small amount of silica gel and loaded on a 24 g pre-packed silica gel column. Eluting the column with ethyl acetate gave 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid [2-(2-hydroxy-ethoxy)-ethylcarbamoyl]-methyl ester as an off-white solid (24 mg, 15% yield). LCMS (ES+) m/z calcd. for $C_{37}H_{41}Cl_2F_2N_4O_7$ [(M+H)+]: 761. found: 761.

Example 75

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (2-{2-[2-(2-hydroxy-ethoxy)-ethoxy]-ethoxy}-ethylcarbamoyl)-methyl ester

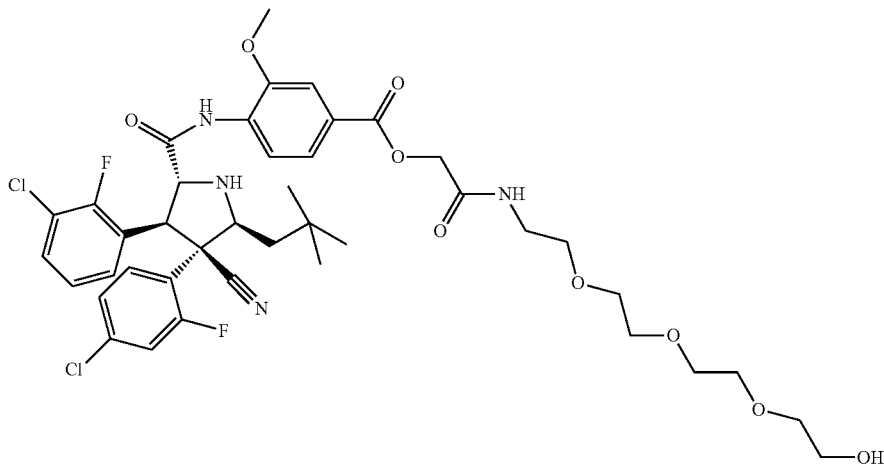

M.W. 849.74 $C_{41}H_{48}Cl_2F_2N_4O_9$

In a 20 mL round-bottomed flask, 2-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxy-benzoyloxy)-acetic acid (Example 69, 150 mg, 152 µL, 222 µmol), HATU (84.6 mg, 222 µmol) and Hunig's base (86.2 mg, 117 µL, 667 µmol) were combined with dry tetrahydrofuran (2 mL) to give an off-white suspension at room temperature. It was stirred for 30 min and the solution became clear. 2-(2-(2-(2-Aminoethoxy)ethoxy)ethoxy)ethanol (43.0 mg, 222 µmol) was added. After stirring at room temperature overnight, the reaction mixture was concentrated. The residue was reconstituted with ethyl acetate. It was washed with water and brine, dried over anhydrous sodium sulfate, filtered and concentrated. The residue was absorbed on small amount of silica gel and loaded on a 24 g pre-packed silica gel column. Eluting the column with 0-10% methanol in ethyl acetate over 20 min gave 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (2-{2-[2-(2-hydroxy-ethoxy)-ethoxy]-ethoxy}-ethylcarbamoyl)-methyl ester as an off-white solid (20 mg, 10% yield). LCMS (ES+) m/z calcd. for $C_{41}H_{48}Cl_2F_2N_4O_9$ [(M+H)+]: 849. found: 849.

Example 76

(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(2-{2-[2-(2-amino-ethoxy)-ethoxy]-ethoxy}-ethylcarbamoyl)-2-methoxy-phenyl]-amide, dimer 4-(4-chloro-2-fluoro-phenyl)-3-(3-chloro-2-fluoro-phenyl)-4-cyano-5-(2,2-dimethyl-propyl)-pyrrolidine-2-carboxylic acid [4-(2-{2-[2-(2-amino-ethoxy)-ethoxy]-ethoxy}-ethyl-carbamoyl)-2-methoxy-phenyl]-amide, dimer as white solid (148 mg, 66% yield). LCMS (ES$^+$) m/z calcd. for $C_{70}H_{74}Cl_4F_4N_8O_9$ [(M+H)$^+$]: 1387. found: 1387.

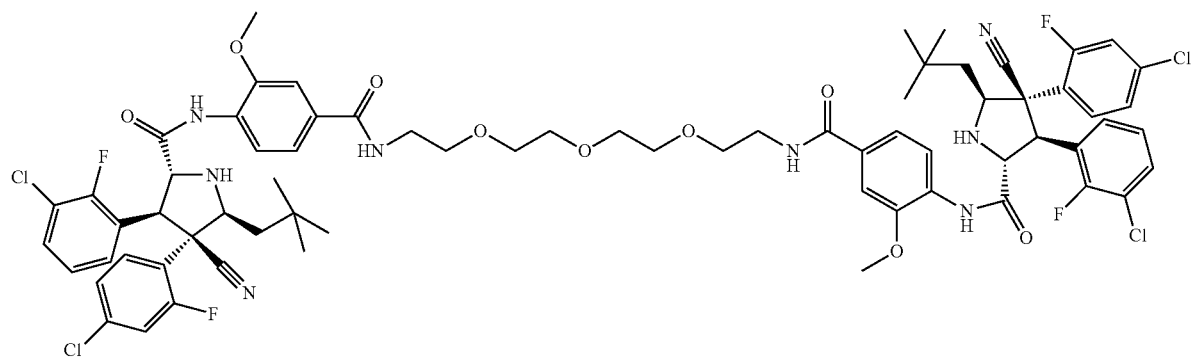

M.W. 1389.21 $C_{70}H_{74}Cl_4F_4N_8O_9$

In a 20 mL round-bottomed flask, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1, 100 mg, 162 μmol), HBTU (61.5 mg, 162 μmol) and Hunig's base (105 mg, 142 μL, 811 μmol) were combined with dry tetrahydrofuran (2 mL) to give an off-white suspension at room temperature. It was stirred at room temperature for 30 min. 1,11-Diamino-3,6,9-trioxaundecane (15.6 mg, 15.2 μL, 81.1 μmol) was added. After stirring at room temperature overnight, the reaction mixture was absorbed on small amount of silica gel, loaded on a 24 g pre-packed silica gel column and eluted with ethyl acetate to give (2R,3S,4R,5S)-

Example 77

(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(2-{2-[2-(2-amino-ethoxy)-ethoxy]-ethoxy}-ethylcarbamoyl)-2-methoxy-phenyl]-amide

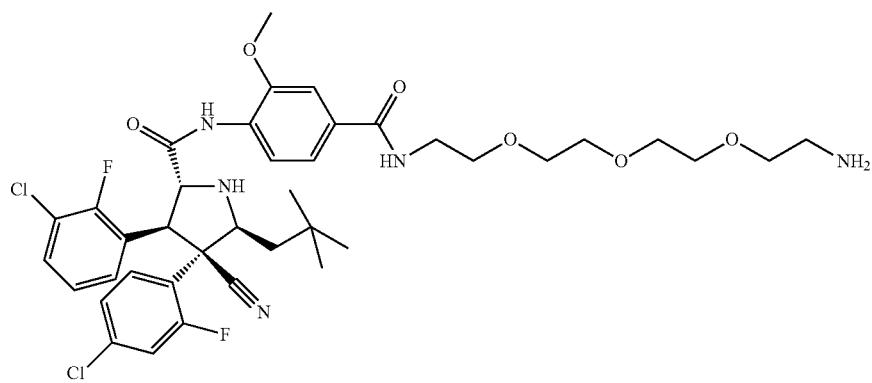

M.W. 790.731 $C_{39}H_{47}Cl_2F_2N_5O_6$

In a 20 mL round-bottomed flask, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxy-benzoic acid (prepared as described in US20100152190A1, 200 mg, 324 μmol) and HATU (136 mg, 357 μmol) combined with dry tetrahydrofuran (2 mL) to give an off-white suspension at room temperature. It was stirred for 30 min at room temperature. The reaction mixture was slowly added dropwise to a solution of 1,11-diamino-3,6,9-trioxaundecane (312 mg, 304 μL, 1.62 mmol) in dry tetrahydrofuran (1.5 mL) at 0° C. The reaction was done after stirring at room temperature for 20 min. It was filtered and injected into Gilson reverse-phase high-performance liquid chromatography for purification. The desired fractions was converted to free base and lyophilized to afford (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid [4-(2-{2-[2-(2-amino-ethoxy)-ethoxy]-ethoxy}-ethylcarbamoyl)-2-methoxy-phenyl]-amide as a white solid (169 mg, 66% yield). LCMS (ES⁺) m/z calcd. for $C_{39}H_{47}Cl_2F_2N_5O_6$ [(M+H)⁺]: 790. found: 790.

Example 78

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid ((S)-1-allyloxycarbonyl-5-tert-butoxycarbonylamino-pentylcarbamoyl)-methyl ester

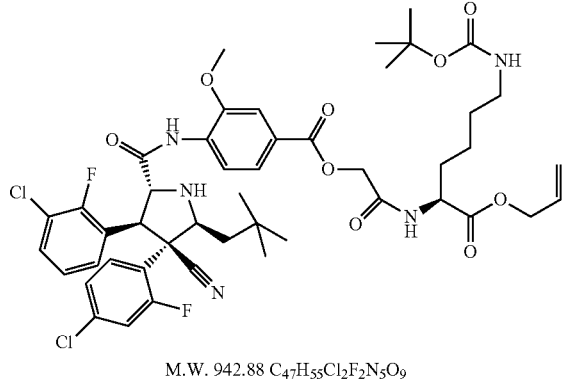 [SMILES: C=CCOC(=O)[C@H](CCCCNC(=O)OC(C)(C)C)NC(=O)COC(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]

M.W. 942.88 $C_{47}H_{55}Cl_2F_2N_5O_9$

In a 20 mL round-bottomed flask, 2-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxy-benzoyloxy)acetic acid (Example 69, 144 mg, 213 μmol), HATU (106 mg, 278 μmol), and Hunig's base (69.0 mg, 93.2 μL, 534 μmol) were combined with dry tetrahydrofuran (2 mL) to give an off-white suspension at room temperature. It was stirred at room temperature for 2 h. Then the mixture of (S)-allyl 2-amino-6-(tert-butoxycarbonylamino)hexanoate hydrochloride (103 mg, 320 μmol) and Hunig's base (55.2 mg, 74.6 μL, 427 μmol) in dry tetrahydrofuran (2 mL) was added. After 20 min, the reaction mixture was purified with high-performance liquid chromatography (C18, eluting with a gradient of 60-80% acetonitrile in water over 10 min) to isolate the desired fractions, which were neutralized with saturated aqueous sodium carbonate solution, extracted with methylene chloride. The methylene chloride layer was washed with water and brine, dried over anhydrous sodium sulfate, filtered and concentrated to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid ((S)-1-allyloxycarbonyl-5-tert-butoxycarbonylamino-pentylcarbamoyl)-methyl ester (16 mg, 8% yield). LCMS (ES⁺) m/z calcd. for $C_{47}H_{56}Cl_2F_2N_5O_9$ [(M+H)⁺]: 942. found: 942.

Example 79

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-1000 amide

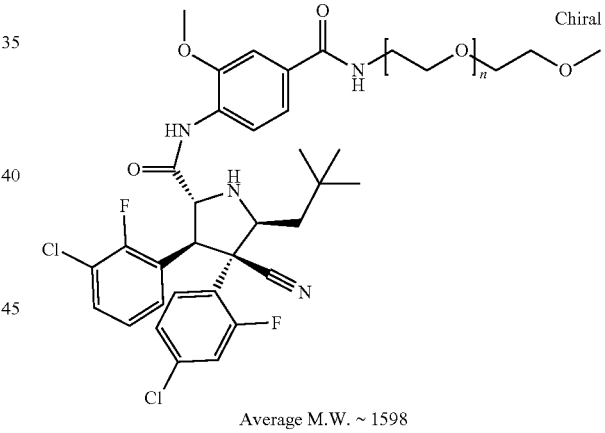

Average M.W. ~ 1598

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with monomethoxy polyethylene glycol-amine 1000 (mPEG-amine 1000) to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-amide 1000.

Example 80

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-1000 ester

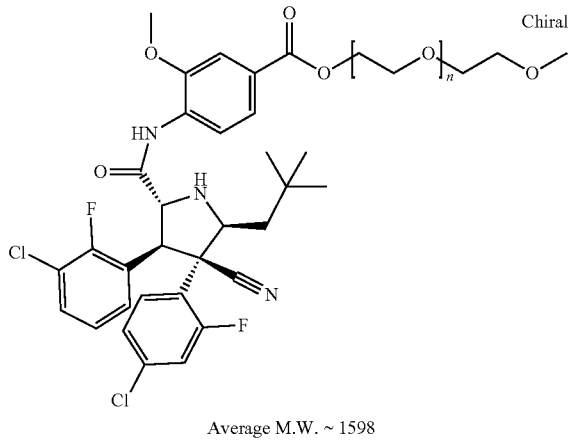

Average M.W. ~ 1598

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with monomethoxy polyethylene glycol 1000 (mPEG-1000) to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-1000 ester.

Example 81

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-2000 amide

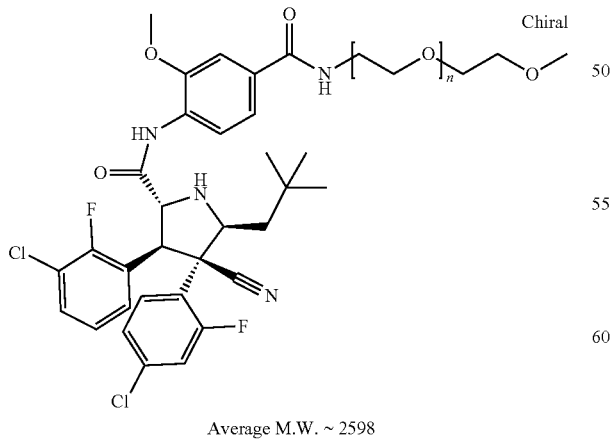

Average M.W. ~ 2598

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with monomethoxy polyethylene glycol-amine 2000 (mPEG-amine 2000) to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-amide 2000.

Example 82

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-2000 ester

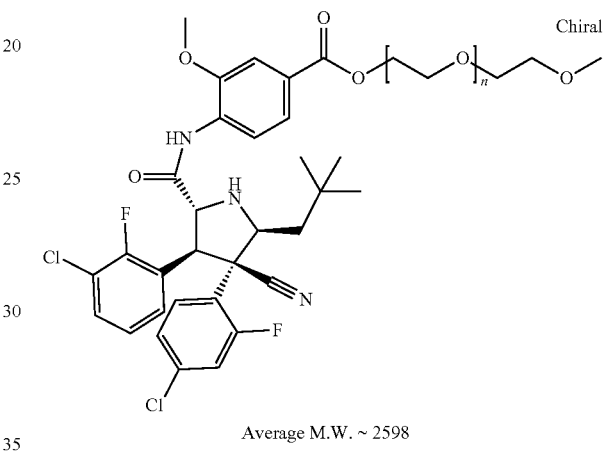

Average M.W. ~ 2598

In a manner similar to the method described in Example 14, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1) was reacted with monomethoxy polyethylene glycol 2000 (mPEG-2000) to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, mPEG-2000 ester.

Example 83

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.02% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM E1-anti-GST and 60 nM streptavidin-APC working solution) in TBS buffer with 0.02% BSA, shake at room temperature for 30 minutes and read using a TRF-capable plate reader at 665 and 615 nm (Victor 5, Perkin ElmerWallac). If not specified, the reagents were purchased from Sigma Chemical Co.

Activity data for some of the Example compounds expressed as $IC_{50}$:bsa:0.02% are as follows:

| Example Number | $IC_{50}$ (uM, 0.02% BSA) |
|---|---|
| 1 | 0.0111 |
| 3 | 0.0144 |
| 4 | 0.00984 |
| 6 | 0.0371 |
| 7 | 0.0146 |
| 8 | 0.00957 |
| 9 | 0.012 |
| 10 | 0.0107 |
| 11 | 0.0117 |
| 12 | 0.00959 |
| 13 | 0.00454 |
| 14 | 0.00675 |
| 16 | 0.0501 |
| 17 | 0.0115 |
| 18 | 0.024 |
| 19 | 0.00558 |
| 20 | 0.00654 |
| 21 | 0.0137 |
| 22 | 0.015 |
| 23 | 0.00934 |
| 24 | 0.0139 |
| 25 | 0.01555 |
| 26 | 0.00867 |
| 27 | 0.0129 |
| 28 | 0.00602 |
| 29 | 0.0167 |
| 30 | 0.0172 |
| 31 | 0.0137 |
| 32 | 0.0164 |
| 33 | 0.01985 |
| 34 | 0.01445 |
| 35 | 0.0125 |
| 36 | 0.00498 |
| 37 | 0.016 |
| 38 | 0.0102 |
| 39 | 0.0365 |
| 40 | 0.0062 |
| 41 | 0.00695 |
| 42 | 0.0222 |
| 43 | 0.0062 |
| 44 | 0.0113 |
| 45 | 0.0105 |
| 46 | 0.0142 |
| 47 | 0.00834 |
| 48 | 0.0135 |
| 49 | 0.0139 |
| 50 | 0.00913 |
| 51 | 0.01 |
| 52 | 0.00995 |
| 53 | 0.0127 |
| 54 | 0.00455 |
| 55 | 0.0091 |
| 56 | 0.00988 |
| 57 | 0.0172 |
| 58 | 0.0144 |
| 59 | 0.0249 |
| 60 | 0.211 |
| 61 | 0.0114 |
| 62 | 0.0293 |
| 63 | 0.0148 |
| 64 | 0.0116 |
| 65 | 0.0129 |
| 66 | 0.00904 |
| 67 | 0.0118 |
| 68 | 0.012 |
| 70 | 0.0564 |
| 71 | 0.00594 |
| 72 | 0.0203 |
| 73 | 0.0196 |
| 74 | 0.0345 |
| 75 | 0.0092 |
| 76 | 0.0643 |
| 77 | 0.00631 |
| 78 | 0.0166 |
| 79 | 0.0345 |
| 80 | 0.0346 |
| 81 | 0.0284 |
| 82 | 0.040 |

What is claimed:

1. A compound selected from the group consisting of:
   2-(Phosphonooxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, trifluoroacetate salt,
   (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(2-hydroxy-1-methyl-ethylcarbamoyl)-2-methoxy-phenyl]-amide,
   4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-diethylamino-ethyl ester,
   4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-methyl-piperidin-4-yl ester,
   4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-methyl-piperidin-4-ylmethyl ester,
   4-{[(2R,3S,4R,5S)-4-(4-Chloro-2-fluoro-phenyl)-3-(3-chloro-2-fluoro-phenyl)-4-cyano-5-(2,2dimethyl-propyl)-pyrrolidine-2-carbonyl]-amino}-3-methoxy-benzoic acid 2-(4-methyl-piperazin-1-yl)-ethyl ester,
   4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid [1,2,3]triazolo[4,5-b]pyridin-3-yl ester,
   4-{[(2R,3S,4R,5S)-4-(4-Chloro-2-fluoro-phenyl)-3-(3-chloro-2-fluoro-phenyl)-4-cyano-5-(2,2dimethyl-propyl)-pyrrolidine-2-carbonyl]-amino}-3-methoxy-benzoic acid 1-methyl-2-morpholin-4-yl-ethyl ester,
   4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-morpholin-4-yl-ethyl ester,
   (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(2-diethylamino-ethylcarbamoyl)-2-methoxy-phenyl]-amide, hydrochloride, and
   4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid dimethylcarbamoylmethyl ester, hydrochloride.

2. A pharmaceutical composition comprising a compound of claim 1 and a therapeutically inert carrier.

3. The compound 2-(Phosphonooxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, trifluoroacetate salt or a pharmaceutically acceptable ester thereof.

* * * * *